US007897566B2

(12) United States Patent
Dong

(10) Patent No.: US 7,897,566 B2
(45) Date of Patent: Mar. 1, 2011

(54) ANALOGUES OF GLP-1

(75) Inventor: Zheng Xin Dong, Holliston, MA (US)

(73) Assignee: Ipsen Pharma S.A.S., Boulogne-Billancourt (FR)

( * ) Notice: Subject to any disclaimer, the term of this patent is extended or adjusted under 35 U.S.C. 154(b) by 1027 days.

(21) Appl. No.: 10/582,534

(22) PCT Filed: Dec. 15, 2004

(86) PCT No.: PCT/US2004/042045
§ 371 (c)(1),
(2), (4) Date: Jun. 9, 2006

(87) PCT Pub. No.: WO2005/058955
PCT Pub. Date: Jun. 30, 2005

(65) Prior Publication Data
US 2007/0042952 A1 Feb. 22, 2007

Related U.S. Application Data

(60) Provisional application No. 60/529,822, filed on Dec. 16, 2003.

(51) Int. Cl.
*A61K 38/26* (2006.01)
(52) U.S. Cl. ............... 514/11.7; 530/324; 530/308; 514/21.3
(58) Field of Classification Search ............ 530/324, 530/308; 514/12, 11.7, 21.3
See application file for complete search history.

(56) References Cited

U.S. PATENT DOCUMENTS

| | | | |
|---|---|---|---|
| 5,512,549 A | 4/1996 | Chen et al. | |
| 5,545,618 A | 8/1996 | Buckley et al. | |
| 5,705,483 A | 1/1998 | Galloway et al. | |
| 6,410,513 B1 | 6/2002 | Galloway et al. | |
| 6,458,924 B2 | 10/2002 | Knudsen et al. | |
| 6,620,910 B1 | 9/2003 | Calas et al. | |
| 6,720,407 B1 | 4/2004 | Hughes et al. | |
| 6,903,186 B1 | 6/2005 | Dong et al. | |
| 2003/0186858 A1 | 10/2003 | Arentsen | |
| 2003/0220243 A1 | 11/2003 | Glaesner et al. | |

FOREIGN PATENT DOCUMENTS

| | | |
|---|---|---|
| EP | 0 733 644 | 9/1993 |
| EP | 0 658 568 | 6/1995 |
| EP | 0 699 686 | 3/1996 |
| EP | 0 708 179 | 4/1996 |
| EP | 0 869 135 | 10/1998 |
| WO | 87/06941 | 11/1987 |
| WO | 91/11457 | 8/1991 |
| WO | 97/29180 | 8/1997 |
| WO | 98/03547 | 1/1998 |
| WO | 98/08871 | 3/1998 |
| WO | 98/19698 | 5/1998 |
| WO | 99/43705 | 9/1999 |
| WO | 99/43706 | 9/1999 |
| WO | 99/43707 | 9/1999 |
| WO | 00/34331 | 6/2000 |
| WO | 00/34332 | 6/2000 |
| WO | 01/35988 | 5/2001 |
| WO | 01/57084 | 8/2001 |
| WO | 01/98331 | 12/2001 |
| WO | 2004/074315 | 9/2004 |

OTHER PUBLICATIONS

Adelhorst, K. et al, "Structure-Activity Studies of Glucagon-Like Peptide-1", 1994, J. of Biological Chem., 269:6275-6278.
Ahren, Bo, et al.; "Effects of Glucagon-Like Peptide-1 on Islet Function and Insulin Sensitivity in Noninsulin-Dependent Diabetes Mellitus"; 1997; Journal of Clinical Endocrinology and Metabolism; 82:473-478.
Deacon, C.F., et al.; "Dipeptidyl peptidase IV resistant analogues of glucagon-like peptide-1 which have extended metabolic stability and improved biological activity"; 1998; Diabetologia; 41:271-278.
Deacon, C.F., et al.; "Dipeptidyl Peptidase IV Inhibition Potentiates the Insulinotropic Effect of Glucagon-Like Peptide 1 in the Anesthetized Pig"; 1998; Diabetes; 47:764-769.
Gutniak, Mark, et al.; "Antidiabetogenic Effect of Glucagon-Like Peptide-1 (7-36) Amide in Normal Subjects and Patients with Diabetes Mellitus"; 1992; The New England Journal of Medicine; 326:1316-1322.
Mentlein, R., et al; "Dipeptidyl-peptidase IV hydrolyses gastric inhibitory polypeptide, Glucagon-like peptide-1 (7-36) amide, peptide histidine methionine and is responsible for their degradation in human serum"; 1993; Biochem; 214:829-835.
Mojsov, S. "Structural requirements for biological activity of glucagon-like peptide I," Int. J. Pep. Prot. Res., 1992, 40:333-343.
Nauck, M.A. et al.; "Effects of subcutaneous glucagon-like peptide 1 (GLP-1 [7-36 amide]) in patients with NIIDM"; 1996; Diabetologia; 82:1546-1553.
Parker, J. C. et al, "Structure-Function Analysis of a Series of Glucagon-Like Peptide-1 Analogs", 1998, J. Peptide Res., 52:398-409.
Rachman, J. et al.; "Near-normalisation of diurnal glucose concentrations by continuous administration of glucagon-like peptide-1 (GLP-1) in subjects with NIDDM"; 1997; Diabetologia; 40:205-211.
Ritzel, U. et al, "A Synthetic Glucagon-Like Peptide-1 Analog With Improved Plasma Stability", 1998, J. of Endocrinology, 159:93-102.
Suzuki, S., et al.; "Comparison of the Effects of Various C-Terminal and N-Terminal Fragment Peptides of Glucagon-Like Peptide-1 on Insulin and Glucagon Release from the Isolated Perfused Rat Pancreas"; 1989; Endocrinology; 125: 3109-3114.
Thorens, Bernard, et al.; "Glucagon-Like Peptide-I and the Control of Insulin Secretion in the Normal State and in NIDDM"; 1993; Diabetes; 42:1219-1225.
Thorens, Bernard, et al.; "Structure and Function of the Glucagon-Like Peptide-1 Receptor"; 1996; Handbook of Experimental Pharmacology; 123:255-273.
Todd, J.F., et al.; "Glucagon-like peptide-1 (GLP-1): a trial of treatment in non-insulin-dependent diabetes mellitus"; 1997; European Journal of Clinical Investigation; 27:533-536.
Dong, J. Z. et al., "Glucagon-like peptide-1 analogs with significantly improved in vivo activity", 2001, Peptides: The Wave of the Future, Michal Lebl and Richard Houghten, Eds., American Peptide Society, p. 670-671.

*Primary Examiner*—David Lukton
(74) *Attorney, Agent, or Firm*—Yankwich & Associates; Tony K. Uhm; Alan F. Feeney

(57) ABSTRACT

Disclosed are peptide analogues of glucagon-like peptide-1, the pharmaceutically-acceptable salts thereof, methods of using such analogues to treat mammals and pharmaceutical compositions useful therefor comprising said analogues.

2 Claims, No Drawings

SEQUENCE LISTING

<160> NUMBER OF SEQ ID NOS: 43

<210> SEQ ID NO 1
<211> LENGTH: 33
<212> TYPE: PRT
<213> ORGANISM: Artificial Sequence

```
<220> FEATURE:
<223> OTHER INFORMATION: GLP-1 Analogue
<220> FEATURE:
<221> NAME/KEY: MISC_FEATURE
<222> LOCATION: (2)..(2)
<223> OTHER INFORMATION: Xaa = alpha-aminoisobutyric acid
<220> FEATURE:
<221> NAME/KEY: MISC_FEATURE
<222> LOCATION: (29)..(29)
<223> OTHER INFORMATION: Xaa = alpha-aminoisobutyric acid
<220> FEATURE:
<221> NAME/KEY: MOD_RES
<222> LOCATION: (33)..(33)
<223> OTHER INFORMATION: AMIDATION

<400> SEQUENCE: 1

His Xaa Glu Gly Thr Phe Thr Ser Asp Val Ser Ser Tyr Leu Glu Gly
 1               5                  10                  15

Gln Ala Ala Arg Glu Phe Ile Ala Phe Leu Val Arg Xaa Arg Pro Ser
            20                  25                  30

Ser

<210> SEQ ID NO 2
<211> LENGTH: 32
<212> TYPE: PRT
<213> ORGANISM: Artificial Sequence
<220> FEATURE:
<223> OTHER INFORMATION: GLP-1 Analogue
<220> FEATURE:
<221> NAME/KEY: MISC_FEATURE
<222> LOCATION: (2)..(2)
<223> OTHER INFORMATION: Xaa = alpha-aminoisobutyric acid
<220> FEATURE:
<221> NAME/KEY: MISC_FEATURE
<222> LOCATION: (29)..(29)
<223> OTHER INFORMATION: Xaa = alpha-aminoisobutyric acid
<220> FEATURE:
<221> NAME/KEY: MISC_FEATURE
<222> LOCATION: (31)..(31)
<223> OTHER INFORMATION: Xaa = alpha-aminoisobutyric acid
<220> FEATURE:
<221> NAME/KEY: MOD_RES
<222> LOCATION: (32)..(32)
<223> OTHER INFORMATION: AMIDATION

<400> SEQUENCE: 2

His Xaa Glu Gly Thr Phe Thr Ser Asp Val Ser Ser Tyr Leu Glu Gly
 1               5                  10                  15

Gln Ala Ala Arg Glu Phe Ile Ala Phe Leu Val Arg Xaa Arg Xaa Asn
            20                  25                  30

<210> SEQ ID NO 3
<211> LENGTH: 32
<212> TYPE: PRT
<213> ORGANISM: Artificial Sequence
<220> FEATURE:
<223> OTHER INFORMATION: GLP-1 Analogue
<220> FEATURE:
<221> NAME/KEY: MISC_FEATURE
<222> LOCATION: (2)..(2)
<223> OTHER INFORMATION: Xaa = alpha-aminoisobutyric acid
<220> FEATURE:
<221> NAME/KEY: MISC_FEATURE
<222> LOCATION: (29)..(29)
<223> OTHER INFORMATION: Xaa = alpha-aminoisobutyric acid
<220> FEATURE:
<221> NAME/KEY: MISC_FEATURE
<222> LOCATION: (31)..(31)
<223> OTHER INFORMATION: Xaa = alpha-aminoisobutyric acid
<220> FEATURE:
<221> NAME/KEY: MOD_RES
<222> LOCATION: (32)..(32)
```

```
<223> OTHER INFORMATION: AMIDATION

<400> SEQUENCE: 3

His Xaa Glu Gly Thr Phe Thr Ser Asp Val Ser Ser Tyr Leu Glu Gly
 1               5                  10                  15

Gln Ala Ala Arg Glu Phe Ile Ala Phe Leu Val Arg Xaa Arg Xaa Ser
            20                  25                  30

<210> SEQ ID NO 4
<211> LENGTH: 32
<212> TYPE: PRT
<213> ORGANISM: Artificial Sequence
<220> FEATURE:
<223> OTHER INFORMATION: GLP-1 Analogue
<220> FEATURE:
<221> NAME/KEY: MISC_FEATURE
<222> LOCATION: (2)..(2)
<223> OTHER INFORMATION: Xaa = alpha-aminoisobutyric acid
<220> FEATURE:
<221> NAME/KEY: MISC_FEATURE
<222> LOCATION: (29)..(29)
<223> OTHER INFORMATION: Xaa = alpha-aminoisobutyric acid
<220> FEATURE:
<221> NAME/KEY: MISC_FEATURE
<222> LOCATION: (31)..(31)
<223> OTHER INFORMATION: Xaa = alpha-aminoisobutyric acid
<220> FEATURE:
<221> NAME/KEY: MOD_RES
<222> LOCATION: (32)..(32)
<223> OTHER INFORMATION: AMIDATION
<220> FEATURE:
<221> NAME/KEY: MISC_FEATURE
<222> LOCATION: (32)..(32)
<223> OTHER INFORMATION: Xaa = gamma-aminobutyric acid

<400> SEQUENCE: 4

His Xaa Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Xaa Arg Xaa Xaa
            20                  25                  30

<210> SEQ ID NO 5
<211> LENGTH: 32
<212> TYPE: PRT
<213> ORGANISM: Artificial Sequence
<220> FEATURE:
<223> OTHER INFORMATION: GLP-1 Analogue
<220> FEATURE:
<221> NAME/KEY: MISC_FEATURE
<222> LOCATION: (2)..(2)
<223> OTHER INFORMATION: Xaa = alpha-aminoisobutyric acid
<220> FEATURE:
<221> NAME/KEY: MISC_FEATURE
<222> LOCATION: (29)..(29)
<223> OTHER INFORMATION: Xaa = alpha-aminoisobutyric acid
<220> FEATURE:
<221> NAME/KEY: MISC_FEATURE
<222> LOCATION: (31)..(31)
<223> OTHER INFORMATION: Xaa = alpha-aminoisobutyric acid
<220> FEATURE:
<221> NAME/KEY: MOD_RES
<222> LOCATION: (32)..(32)
<223> OTHER INFORMATION: AMIDATION

<400> SEQUENCE: 5

His Xaa Glu Gly Thr Phe Thr Ser Asp Val Ser Ser Tyr Leu Glu Gly
 1               5                  10                  15

Gln Ala Ala Arg Glu Phe Ile Ala Phe Leu Val Arg Xaa Arg Xaa His
            20                  25                  30
```

```
<210> SEQ ID NO 6
<211> LENGTH: 32
<212> TYPE: PRT
<213> ORGANISM: Artificial Sequence
<220> FEATURE:
<223> OTHER INFORMATION: GLP-1 Analogue
<220> FEATURE:
<221> NAME/KEY: MISC_FEATURE
<222> LOCATION: (2)..(2)
<223> OTHER INFORMATION: Xaa = alpha-aminoisobutyric acid
<220> FEATURE:
<221> NAME/KEY: MISC_FEATURE
<222> LOCATION: (29)..(29)
<223> OTHER INFORMATION: Xaa = alpha-aminoisobutyric acid
<220> FEATURE:
<221> NAME/KEY: MISC_FEATURE
<222> LOCATION: (31)..(31)
<223> OTHER INFORMATION: Xaa = Beta-Ala
<220> FEATURE:
<221> NAME/KEY: MOD_RES
<222> LOCATION: (32)..(32)
<223> OTHER INFORMATION: AMIDATION

<400> SEQUENCE: 6

His Xaa Glu Gly Thr Phe Thr Ser Asp Val Ser Ser Tyr Leu Glu Gly
1               5                   10                  15

Gln Ala Ala Arg Glu Phe Ile Ala Phe Leu Val Arg Xaa Arg Xaa His
            20                  25                  30

<210> SEQ ID NO 7
<211> LENGTH: 32
<212> TYPE: PRT
<213> ORGANISM: Artificial Sequence
<220> FEATURE:
<223> OTHER INFORMATION: GLP-1 Analogue
<220> FEATURE:
<221> NAME/KEY: MISC_FEATURE
<222> LOCATION: (2)..(2)
<223> OTHER INFORMATION: Xaa = alpha-aminoisobutyric acid
<220> FEATURE:
<221> NAME/KEY: MISC_FEATURE
<222> LOCATION: (29)..(29)
<223> OTHER INFORMATION: Xaa = alpha-aminoisobutyric acid
<220> FEATURE:
<221> NAME/KEY: MISC_FEATURE
<222> LOCATION: (31)..(31)
<223> OTHER INFORMATION: Xaa = alpha-aminoisobutyric acid
<220> FEATURE:
<221> NAME/KEY: MOD_RES
<222> LOCATION: (32)..(32)
<223> OTHER INFORMATION: AMIDATION
<220> FEATURE:
<221> NAME/KEY: MISC_FEATURE
<222> LOCATION: (32)..(32)
<223> OTHER INFORMATION: Xaa = D-His

<400> SEQUENCE: 7

His Xaa Glu Gly Thr Phe Thr Ser Asp Val Ser Ser Tyr Leu Glu Gly
1               5                   10                  15

Gln Ala Ala Arg Glu Phe Ile Ala Trp Leu Val Arg Xaa Arg Xaa Xaa
            20                  25                  30

<210> SEQ ID NO 8
<211> LENGTH: 32
<212> TYPE: PRT
<213> ORGANISM: Artificial Sequence
<220> FEATURE:
<223> OTHER INFORMATION: GLP-1 Analogue
<220> FEATURE:
<221> NAME/KEY: MISC_FEATURE
<222> LOCATION: (2)..(2)
<223> OTHER INFORMATION: Xaa = alpha-aminoisobutyric acid
<220> FEATURE:
```

```
<221> NAME/KEY: MISC_FEATURE
<222> LOCATION: (29)..(29)
<223> OTHER INFORMATION: Xaa = alpha-aminoisobutyric acid
<220> FEATURE:
<221> NAME/KEY: MISC_FEATURE
<222> LOCATION: (31)..(31)
<223> OTHER INFORMATION: Xaa = alpha-aminoisobutyric acid
<220> FEATURE:
<221> NAME/KEY: MOD_RES
<222> LOCATION: (32)..(32)
<223> OTHER INFORMATION: AMIDATION
<220> FEATURE:
<221> NAME/KEY: MISC_FEATURE
<222> LOCATION: (32)..(32)
<223> OTHER INFORMATION: Xaa = Beta-Ala

<400> SEQUENCE: 8

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Lys Xaa Arg Xaa Xaa
            20                  25                  30

<210> SEQ ID NO 9
<211> LENGTH: 32
<212> TYPE: PRT
<213> ORGANISM: Artificial Sequence
<220> FEATURE:
<223> OTHER INFORMATION: GLP-1 Analogue
<220> FEATURE:
<221> NAME/KEY: MISC_FEATURE
<222> LOCATION: (2)..(2)
<223> OTHER INFORMATION: Xaa = alpha-aminoisobutyric acid
<220> FEATURE:
<221> NAME/KEY: MISC_FEATURE
<222> LOCATION: (29)..(29)
<223> OTHER INFORMATION: Xaa = alpha-aminoisobutyric acid
<220> FEATURE:
<221> NAME/KEY: MISC_FEATURE
<222> LOCATION: (31)..(31)
<223> OTHER INFORMATION: Xaa = Beta-Ala
<220> FEATURE:
<221> NAME/KEY: MOD_RES
<222> LOCATION: (32)..(32)
<223> OTHER INFORMATION: AMIDATION

<400> SEQUENCE: 9

His Xaa Glu Gly Thr Phe Thr Ser Asp Val Ser Ser Tyr Leu Glu Gly
1               5                   10                  15

Gln Ala Ala Arg Glu Phe Ile Ala Trp Leu Val Arg Xaa Arg Xaa His
            20                  25                  30

<210> SEQ ID NO 10
<211> LENGTH: 32
<212> TYPE: PRT
<213> ORGANISM: Artificial Sequence
<220> FEATURE:
<223> OTHER INFORMATION: GLP-1 Analogue
<220> FEATURE:
<221> NAME/KEY: MISC_FEATURE
<222> LOCATION: (2)..(2)
<223> OTHER INFORMATION: Xaa = alpha-aminoisobutyric acid
<220> FEATURE:
<221> NAME/KEY: MISC_FEATURE
<222> LOCATION: (29)..(29)
<223> OTHER INFORMATION: Xaa = alpha-aminoisobutyric acid
<220> FEATURE:
<221> NAME/KEY: MISC_FEATURE
<222> LOCATION: (31)..(31)
<223> OTHER INFORMATION: Xaa = alpha-aminoisobutyric acid
<220> FEATURE:
<221> NAME/KEY: MOD_RES
<222> LOCATION: (32)..(32)
<223> OTHER INFORMATION: AMIDATION
```

<400> SEQUENCE: 10

His Xaa Glu Gly Thr Phe Thr Ser Asp Val Ser Ser Tyr Leu Glu Gly
1               5                   10                  15

Gln Ala Ala Arg Glu Phe Ile Ala Phe Leu Val Arg Xaa Arg Xaa Gly
            20                  25                  30

<210> SEQ ID NO 11
<211> LENGTH: 32
<212> TYPE: PRT
<213> ORGANISM: Artificial Sequence
<220> FEATURE:
<223> OTHER INFORMATION: GLP-1 Analogue
<220> FEATURE:
<221> NAME/KEY: MISC_FEATURE
<222> LOCATION: (2)..(2)
<223> OTHER INFORMATION: Xaa = alpha-aminoisobutyric acid
<220> FEATURE:
<221> NAME/KEY: MISC_FEATURE
<222> LOCATION: (29)..(29)
<223> OTHER INFORMATION: Xaa = alpha-aminoisobutyric acid
<220> FEATURE:
<221> NAME/KEY: MISC_FEATURE
<222> LOCATION: (31)..(31)
<223> OTHER INFORMATION: Xaa = alpha-aminoisobutyric acid
<220> FEATURE:
<221> NAME/KEY: MOD_RES
<222> LOCATION: (32)..(32)
<223> OTHER INFORMATION: AMIDATION

<400> SEQUENCE: 11

His Xaa Glu Gly Thr Phe Thr Ser Asp Val Ser Ser Tyr Leu Glu Gly
1               5                   10                  15

Gln Ala Ala Arg Glu Phe Ile Ala Trp Leu Val Arg Xaa Arg Xaa Gly
            20                  25                  30

<210> SEQ ID NO 12
<211> LENGTH: 32
<212> TYPE: PRT
<213> ORGANISM: Artificial Sequence
<220> FEATURE:
<223> OTHER INFORMATION: GLP-1 Analogue
<220> FEATURE:
<221> NAME/KEY: MISC_FEATURE
<222> LOCATION: (2)..(2)
<223> OTHER INFORMATION: Xaa = alpha-aminoisobutyric acid
<220> FEATURE:
<221> NAME/KEY: MISC_FEATURE
<222> LOCATION: (29)..(29)
<223> OTHER INFORMATION: Xaa = alpha-aminoisobutyric acid
<220> FEATURE:
<221> NAME/KEY: MISC_FEATURE
<222> LOCATION: (31)..(31)
<223> OTHER INFORMATION: Xaa = alpha-aminoisobutyric acid
<220> FEATURE:
<221> NAME/KEY: MOD_RES
<222> LOCATION: (32)..(32)
<223> OTHER INFORMATION: AMIDATION
<220> FEATURE:
<221> NAME/KEY: MISC_FEATURE
<222> LOCATION: (32)..(32)
<223> OTHER INFORMATION: Xaa = Beta-Ala

<400> SEQUENCE: 12

His Xaa Glu Gly Thr Phe Thr Ser Asp Val Ser Ser Tyr Leu Glu Gly
1               5                   10                  15

Gln Ala Ala Arg Glu Phe Ile Ala Trp Leu Val Arg Xaa Arg Xaa Xaa
            20                  25                  30

<210> SEQ ID NO 13

```
<211> LENGTH: 32
<212> TYPE: PRT
<213> ORGANISM: Artificial Sequence
<220> FEATURE:
<223> OTHER INFORMATION: GLP-1 Analogue
<220> FEATURE:
<221> NAME/KEY: MISC_FEATURE
<222> LOCATION: (2)..(2)
<223> OTHER INFORMATION: Xaa = alpha-aminoisobutyric acid
<220> FEATURE:
<221> NAME/KEY: MISC_FEATURE
<222> LOCATION: (29)..(29)
<223> OTHER INFORMATION: Xaa = alpha-aminoisobutyric acid
<220> FEATURE:
<221> NAME/KEY: MISC_FEATURE
<222> LOCATION: (31)..(31)
<223> OTHER INFORMATION: Xaa = alpha-aminoisobutyric acid
<220> FEATURE:
<221> NAME/KEY: MOD_RES
<222> LOCATION: (32)..(32)
<223> OTHER INFORMATION: AMIDATION
<220> FEATURE:
<221> NAME/KEY: MISC_FEATURE
<222> LOCATION: (32)..(32)
<223> OTHER INFORMATION: Xaa = Gamma-aminobutyric acid

<400> SEQUENCE: 13

His Xaa Glu Gly Thr Phe Thr Ser Asp Val Ser Ser Tyr Leu Glu Gly
1               5                   10                  15

Gln Ala Ala Arg Glu Phe Ile Ala Trp Leu Val Arg Xaa Arg Xaa Xaa
            20                  25                  30

<210> SEQ ID NO 14
<211> LENGTH: 32
<212> TYPE: PRT
<213> ORGANISM: Artificial Sequence
<220> FEATURE:
<223> OTHER INFORMATION: GLP-1 Analogue
<220> FEATURE:
<221> NAME/KEY: MISC_FEATURE
<222> LOCATION: (2)..(2)
<223> OTHER INFORMATION: Xaa = alpha-aminoisobutyric acid
<220> FEATURE:
<221> NAME/KEY: MISC_FEATURE
<222> LOCATION: (29)..(29)
<223> OTHER INFORMATION: Xaa = alpha-aminoisobutyric acid
<220> FEATURE:
<221> NAME/KEY: MISC_FEATURE
<222> LOCATION: (31)..(31)
<223> OTHER INFORMATION: Xaa = alpha-aminoisobutyric acid
<220> FEATURE:
<221> NAME/KEY: MOD_RES
<222> LOCATION: (32)..(32)
<223> OTHER INFORMATION: AMIDATION

<400> SEQUENCE: 14

His Xaa Glu Gly Thr Phe Thr Ser Asp Val Ser Ser Tyr Leu Glu Gly
1               5                   10                  15

Gln Ala Ala Lys Glu Phe Ile Ala Phe Leu Val Arg Xaa Arg Xaa His
            20                  25                  30

<210> SEQ ID NO 15
<211> LENGTH: 32
<212> TYPE: PRT
<213> ORGANISM: Artificial Sequence
<220> FEATURE:
<223> OTHER INFORMATION: GLP-1 Analogue
<220> FEATURE:
<221> NAME/KEY: MISC_FEATURE
<222> LOCATION: (2)..(2)
<223> OTHER INFORMATION: Xaa = alpha-aminoisobutyric acid
<220> FEATURE:
<221> NAME/KEY: MISC_FEATURE
```

```
<222> LOCATION: (29)..(29)
<223> OTHER INFORMATION: Xaa = alpha-aminoisobutyric acid
<220> FEATURE:
<221> NAME/KEY: MISC_FEATURE
<222> LOCATION: (31)..(31)
<223> OTHER INFORMATION: Xaa = alpha-aminoisobutyric acid
<220> FEATURE:
<221> NAME/KEY: MOD_RES
<222> LOCATION: (32)..(32)
<223> OTHER INFORMATION: AMIDATION

<400> SEQUENCE: 15

His Xaa Glu Gly Thr Phe Thr Ser Asp Val Ser Ser Tyr Leu Glu Gly
1               5                   10                  15

Gln Ala Ala Arg Glu Phe Ile Ala Trp Leu Val Arg Xaa Arg Xaa His
            20                  25                  30

<210> SEQ ID NO 16
<211> LENGTH: 32
<212> TYPE: PRT
<213> ORGANISM: Artificial Sequence
<220> FEATURE:
<223> OTHER INFORMATION: GLP-1 Analogue
<220> FEATURE:
<221> NAME/KEY: MISC_FEATURE
<222> LOCATION: (2)..(2)
<223> OTHER INFORMATION: Xaa = alpha-aminoisobutyric acid
<220> FEATURE:
<221> NAME/KEY: MISC_FEATURE
<222> LOCATION: (29)..(29)
<223> OTHER INFORMATION: Xaa = alpha-aminoisobutyric acid
<220> FEATURE:
<221> NAME/KEY: MISC_FEATURE
<222> LOCATION: (31)..(31)
<223> OTHER INFORMATION: Xaa = alpha-aminoisobutyric acid
<220> FEATURE:
<221> NAME/KEY: MOD_RES
<222> LOCATION: (32)..(32)
<223> OTHER INFORMATION: AMIDATION
<220> FEATURE:
<221> NAME/KEY: MISC_FEATURE
<222> LOCATION: (32)..(32)
<223> OTHER INFORMATION: Xaa = gamma-aminobutyric acid

<400> SEQUENCE: 16

His Xaa Glu Gly Thr Phe Thr Ser Asp Val Ser Ser Tyr Leu Glu Gly
1               5                   10                  15

Gln Ala Ala Arg Glu Phe Ile Ala Phe Leu Val Arg Xaa Arg Xaa Xaa
            20                  25                  30

<210> SEQ ID NO 17
<211> LENGTH: 32
<212> TYPE: PRT
<213> ORGANISM: Artificial Sequence
<220> FEATURE:
<223> OTHER INFORMATION: GLP-1 Analogue
<220> FEATURE:
<221> NAME/KEY: MISC_FEATURE
<222> LOCATION: (2)..(2)
<223> OTHER INFORMATION: Xaa = alpha-aminoisobutyric acid
<220> FEATURE:
<221> NAME/KEY: MISC_FEATURE
<222> LOCATION: (29)..(29)
<223> OTHER INFORMATION: Xaa = alpha-aminoisobutyric acid
<220> FEATURE:
<221> NAME/KEY: MISC_FEATURE
<222> LOCATION: (31)..(31)
<223> OTHER INFORMATION: Xaa = alpha-aminoisobutyric acid
<220> FEATURE:
<221> NAME/KEY: MOD_RES
<222> LOCATION: (32)..(32)
<223> OTHER INFORMATION: AMIDATION
<220> FEATURE:
```

```
<221> NAME/KEY: MISC_FEATURE
<222> LOCATION: (32)..(32)
<223> OTHER INFORMATION: Xaa = 5-aminovaleric acid

<400> SEQUENCE: 17

His Xaa Glu Gly Thr Phe Thr Ser Asp Val Ser Ser Tyr Leu Glu Gly
1               5                   10                  15

Gln Ala Ala Arg Glu Phe Ile Ala Phe Leu Val Arg Xaa Arg Xaa Xaa
            20                  25                  30

<210> SEQ ID NO 18
<211> LENGTH: 32
<212> TYPE: PRT
<213> ORGANISM: Artificial Sequence
<220> FEATURE:
<223> OTHER INFORMATION: GLP-1 Analogue
<220> FEATURE:
<221> NAME/KEY: MISC_FEATURE
<222> LOCATION: (2)..(2)
<223> OTHER INFORMATION: Xaa = alpha-aminoisobutyric acid
<220> FEATURE:
<221> NAME/KEY: MISC_FEATURE
<222> LOCATION: (29)..(29)
<223> OTHER INFORMATION: Xaa = alpha-aminoisobutyric acid
<220> FEATURE:
<221> NAME/KEY: MISC_FEATURE
<222> LOCATION: (31)..(31)
<223> OTHER INFORMATION: Xaa = alpha-aminoisobutyric acid
<220> FEATURE:
<221> NAME/KEY: MOD_RES
<222> LOCATION: (32)..(32)
<223> OTHER INFORMATION: AMIDATION
<220> FEATURE:
<221> NAME/KEY: MISC_FEATURE
<222> LOCATION: (32)..(32)
<223> OTHER INFORMATION: Xaa = 5-aminovaleric acid

<400> SEQUENCE: 18

His Xaa Glu Gly Thr Phe Thr Ser Asp Val Ser Ser Tyr Leu Glu Gly
1               5                   10                  15

Gln Ala Ala Arg Glu Phe Ile Ala Trp Leu Val Arg Xaa Arg Xaa Xaa
            20                  25                  30

<210> SEQ ID NO 19
<211> LENGTH: 32
<212> TYPE: PRT
<213> ORGANISM: Artificial Sequence
<220> FEATURE:
<223> OTHER INFORMATION: GLP-1 Analogue
<220> FEATURE:
<221> NAME/KEY: MISC_FEATURE
<222> LOCATION: (2)..(2)
<223> OTHER INFORMATION: Xaa = alpha-aminoisobutyric acid
<220> FEATURE:
<221> NAME/KEY: MISC_FEATURE
<222> LOCATION: (29)..(29)
<223> OTHER INFORMATION: Xaa = alpha-aminoisobutyric acid
<220> FEATURE:
<221> NAME/KEY: MISC_FEATURE
<222> LOCATION: (31)..(31)
<223> OTHER INFORMATION: Xaa = alpha-aminoisobutyric acid
<220> FEATURE:
<221> NAME/KEY: MOD_RES
<222> LOCATION: (32)..(32)
<223> OTHER INFORMATION: AMIDATION
<220> FEATURE:
<221> NAME/KEY: MISC_FEATURE
<222> LOCATION: (32)..(32)
<223> OTHER INFORMATION: Xaa = D-His

<400> SEQUENCE: 19

His Xaa Glu Gly Thr Phe Thr Ser Asp Val Ser Ser Tyr Leu Glu Gly
```

```
                1               5                  10                  15
Gln Ala Ala Lys Glu Phe Ile Ala Phe Leu Val Arg Xaa Arg Xaa Xaa
                20                  25                  30

<210> SEQ ID NO 20
<211> LENGTH: 32
<212> TYPE: PRT
<213> ORGANISM: Artificial Sequence
<220> FEATURE:
<223> OTHER INFORMATION: GLP-1 Analogue
<220> FEATURE:
<221> NAME/KEY: MISC_FEATURE
<222> LOCATION: (2)..(2)
<223> OTHER INFORMATION: Xaa = alpha-aminoisobutyric acid
<220> FEATURE:
<221> NAME/KEY: MISC_FEATURE
<222> LOCATION: (29)..(29)
<223> OTHER INFORMATION: Xaa = alpha-aminoisobutyric acid
<220> FEATURE:
<221> NAME/KEY: MISC_FEATURE
<222> LOCATION: (31)..(31)
<223> OTHER INFORMATION: Xaa = alpha-aminoisobutyric acid
<220> FEATURE:
<221> NAME/KEY: MOD_RES
<222> LOCATION: (32)..(32)
<223> OTHER INFORMATION: AMIDATION

<400> SEQUENCE: 20

His Xaa Glu Gly Thr Phe Thr Ser Asp Val Ser Ser Tyr Leu Glu Gly
1               5                  10                  15

Gln Ala Ala Lys Glu Phe Ile Ala Phe Leu Val Arg Xaa Arg Xaa Gly
                20                  25                  30

<210> SEQ ID NO 21
<211> LENGTH: 32
<212> TYPE: PRT
<213> ORGANISM: Artificial Sequence
<220> FEATURE:
<223> OTHER INFORMATION: GLP-1 Analogue
<220> FEATURE:
<221> NAME/KEY: MISC_FEATURE
<222> LOCATION: (2)..(2)
<223> OTHER INFORMATION: Xaa = alpha-aminoisobutyric acid
<220> FEATURE:
<221> NAME/KEY: MISC_FEATURE
<222> LOCATION: (29)..(29)
<223> OTHER INFORMATION: Xaa = alpha-aminoisobutyric acid
<220> FEATURE:
<221> NAME/KEY: MISC_FEATURE
<222> LOCATION: (31)..(31)
<223> OTHER INFORMATION: Xaa = alpha-aminoisobutyric acid
<220> FEATURE:
<221> NAME/KEY: MOD_RES
<222> LOCATION: (32)..(32)
<223> OTHER INFORMATION: AMIDATION

<400> SEQUENCE: 21

His Xaa Glu Gly Thr Phe Thr Ser Asp Val Ser Ser Tyr Leu Glu Gly
1               5                  10                  15

Gln Ala Ala Lys Glu Phe Ile Ala Trp Leu Val Lys Xaa Arg Xaa Gly
                20                  25                  30

<210> SEQ ID NO 22
<211> LENGTH: 32
<212> TYPE: PRT
<213> ORGANISM: Artificial Sequence
<220> FEATURE:
<223> OTHER INFORMATION: GLP-1 Analogue
<220> FEATURE:
<221> NAME/KEY: MISC_FEATURE
<222> LOCATION: (2)..(2)
```

```
<223> OTHER INFORMATION: Xaa = alpha-aminoisobutyric acid
<220> FEATURE:
<221> NAME/KEY: MISC_FEATURE
<222> LOCATION: (29)..(29)
<223> OTHER INFORMATION: Xaa = alpha-aminoisobutyric acid
<220> FEATURE:
<221> NAME/KEY: MISC_FEATURE
<222> LOCATION: (31)..(31)
<223> OTHER INFORMATION: Xaa = alpha-aminoisobutyric acid
<220> FEATURE:
<221> NAME/KEY: MOD_RES
<222> LOCATION: (32)..(32)
<223> OTHER INFORMATION: AMIDATION
<220> FEATURE:
<221> NAME/KEY: MISC_FEATURE
<222> LOCATION: (32)..(32)
<223> OTHER INFORMATION: Xaa = D-His

<400> SEQUENCE: 22

His Xaa Glu Gly Thr Phe Thr Ser Asp Val Ser Ser Tyr Leu Glu Gly
 1               5                  10                  15

Gln Ala Ala Arg Glu Phe Ile Ala Phe Leu Val Arg Xaa Arg Xaa Xaa
            20                  25                  30

<210> SEQ ID NO 23
<211> LENGTH: 32
<212> TYPE: PRT
<213> ORGANISM: Artificial Sequence
<220> FEATURE:
<223> OTHER INFORMATION: GLP-1 Analogue
<220> FEATURE:
<221> NAME/KEY: MISC_FEATURE
<222> LOCATION: (2)..(2)
<223> OTHER INFORMATION: Xaa = alpha-aminoisobutyric acid
<220> FEATURE:
<221> NAME/KEY: MISC_FEATURE
<222> LOCATION: (29)..(29)
<223> OTHER INFORMATION: Xaa = alpha-aminoisobutyric acid
<220> FEATURE:
<221> NAME/KEY: MISC_FEATURE
<222> LOCATION: (31)..(31)
<223> OTHER INFORMATION: Xaa = Beta-Ala
<220> FEATURE:
<221> NAME/KEY: MOD_RES
<222> LOCATION: (32)..(32)
<223> OTHER INFORMATION: AMIDATION
<220> FEATURE:
<221> NAME/KEY: MISC_FEATURE
<222> LOCATION: (32)..(32)
<223> OTHER INFORMATION: Xaa = D-His

<400> SEQUENCE: 23

His Xaa Glu Gly Thr Phe Thr Ser Asp Val Ser Ser Tyr Leu Glu Gly
 1               5                  10                  15

Gln Ala Ala Arg Glu Phe Ile Ala Phe Leu Val Arg Xaa Arg Xaa Xaa
            20                  25                  30

<210> SEQ ID NO 24
<211> LENGTH: 32
<212> TYPE: PRT
<213> ORGANISM: Artificial Sequence
<220> FEATURE:
<223> OTHER INFORMATION: GLP-1 Analogue
<220> FEATURE:
<221> NAME/KEY: MISC_FEATURE
<222> LOCATION: (2)..(2)
<223> OTHER INFORMATION: Xaa = alpha-aminoisobutyric acid
<220> FEATURE:
<221> NAME/KEY: MISC_FEATURE
<222> LOCATION: (29)..(29)
<223> OTHER INFORMATION: Xaa = alpha-aminoisobutyric acid
<220> FEATURE:
<221> NAME/KEY: MISC_FEATURE
```

```
<222> LOCATION: (31)..(31)
<223> OTHER INFORMATION: Xaa = alpha-aminoisobutyric acid
<220> FEATURE:
<221> NAME/KEY: MOD_RES
<222> LOCATION: (32)..(32)
<223> OTHER INFORMATION: AMIDATION
<220> FEATURE:
<221> NAME/KEY: MISC_FEATURE
<222> LOCATION: (32)..(32)
<223> OTHER INFORMATION: Xaa = Beta-Ala

<400> SEQUENCE: 24

His Xaa Glu Gly Thr Phe Thr Ser Asp Val Ser Ser Tyr Leu Glu Gly
1               5                   10                  15

Gln Ala Ala Arg Glu Phe Ile Ala Phe Leu Val Arg Xaa Arg Xaa Xaa
            20                  25                  30

<210> SEQ ID NO 25
<211> LENGTH: 32
<212> TYPE: PRT
<213> ORGANISM: Artificial Sequence
<220> FEATURE:
<223> OTHER INFORMATION: GLP-1 Analogue
<220> FEATURE:
<221> NAME/KEY: MISC_FEATURE
<222> LOCATION: (2)..(2)
<223> OTHER INFORMATION: Xaa = alpha-aminoisobutyric acid
<220> FEATURE:
<221> NAME/KEY: MISC_FEATURE
<222> LOCATION: (29)..(29)
<223> OTHER INFORMATION: Xaa = alpha-aminoisobutyric acid
<220> FEATURE:
<221> NAME/KEY: MISC_FEATURE
<222> LOCATION: (31)..(32)
<223> OTHER INFORMATION: Xaa = Beta-Ala
<220> FEATURE:
<221> NAME/KEY: MOD_RES
<222> LOCATION: (32)..(32)
<223> OTHER INFORMATION: AMIDATION

<400> SEQUENCE: 25

His Xaa Glu Gly Thr Phe Thr Ser Asp Val Ser Ser Tyr Leu Glu Gly
1               5                   10                  15

Gln Ala Ala Arg Glu Phe Ile Ala Phe Leu Val Arg Xaa Arg Xaa Xaa
            20                  25                  30

<210> SEQ ID NO 26
<211> LENGTH: 32
<212> TYPE: PRT
<213> ORGANISM: Artificial Sequence
<220> FEATURE:
<223> OTHER INFORMATION: GLP-1 Analogue
<220> FEATURE:
<221> NAME/KEY: MISC_FEATURE
<222> LOCATION: (2)..(2)
<223> OTHER INFORMATION: Xaa = alpha-aminoisobutyric acid
<220> FEATURE:
<221> NAME/KEY: MISC_FEATURE
<222> LOCATION: (29)..(29)
<223> OTHER INFORMATION: Xaa = alpha-aminoisobutyric acid
<220> FEATURE:
<221> NAME/KEY: MISC_FEATURE
<222> LOCATION: (31)..(31)
<223> OTHER INFORMATION: Xaa = alpha-aminoisobutyric acid
<220> FEATURE:
<221> NAME/KEY: MOD_RES
<222> LOCATION: (32)..(32)
<223> OTHER INFORMATION: AMIDATION
<220> FEATURE:
<221> NAME/KEY: MISC_FEATURE
<222> LOCATION: (32)..(32)
<223> OTHER INFORMATION: Xaa = Beta-Ala
```

```
<400> SEQUENCE: 26

His Xaa Glu Gly Thr Phe Thr Ser Asp Val Ser Ser Tyr Leu Glu Gly
1               5                   10                  15

Gln Ala Ala Lys Glu Phe Ile Ala Phe Leu Val Arg Xaa Arg Xaa Xaa
            20                  25                  30

<210> SEQ ID NO 27
<211> LENGTH: 32
<212> TYPE: PRT
<213> ORGANISM: Artificial Sequence
<220> FEATURE:
<223> OTHER INFORMATION: GLP-1 Analogue
<220> FEATURE:
<221> NAME/KEY: MISC_FEATURE
<222> LOCATION: (2)..(2)
<223> OTHER INFORMATION: Xaa = alpha-aminoisobutyric acid
<220> FEATURE:
<221> NAME/KEY: MISC_FEATURE
<222> LOCATION: (29)..(29)
<223> OTHER INFORMATION: Xaa = alpha-aminoisobutyric acid
<220> FEATURE:
<221> NAME/KEY: MISC_FEATURE
<222> LOCATION: (31)..(31)
<223> OTHER INFORMATION: Xaa = alpha-aminoisobutyric acid
<220> FEATURE:
<221> NAME/KEY: MOD_RES
<222> LOCATION: (32)..(32)
<223> OTHER INFORMATION: AMIDATION
<220> FEATURE:
<221> NAME/KEY: MISC_FEATURE
<222> LOCATION: (32)..(32)
<223> OTHER INFORMATION: Xaa = Gama-aminobutyric acid

<400> SEQUENCE: 27

His Xaa Glu Gly Thr Phe Thr Ser Asp Val Ser Ser Tyr Leu Glu Gly
1               5                   10                  15

Gln Ala Ala Lys Glu Phe Ile Ala Phe Leu Val Arg Xaa Arg Xaa Xaa
            20                  25                  30

<210> SEQ ID NO 28
<211> LENGTH: 30
<212> TYPE: PRT
<213> ORGANISM: Artificial Sequence
<220> FEATURE:
<223> OTHER INFORMATION: GLP-1 Analogue
<220> FEATURE:
<221> NAME/KEY: MISC_FEATURE
<222> LOCATION: (1)..(1)
<223> OTHER INFORMATION: Xaa = (4-hydroxyphenyl)propionic acid
<220> FEATURE:
<221> NAME/KEY: MOD_RES
<222> LOCATION: (30)..(30)
<223> OTHER INFORMATION: AMIDATION

<400> SEQUENCE: 28

Xaa Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 29
<211> LENGTH: 30
<212> TYPE: PRT
<213> ORGANISM: Artificial Sequence
<220> FEATURE:
<223> OTHER INFORMATION: GLP-1 Analogue
<220> FEATURE:
<221> NAME/KEY: MISC_FEATURE
<222> LOCATION: (1)..(1)
<223> OTHER INFORMATION: Xaa = (3-hydroxyphenyl)propionic acid
```

```
<220> FEATURE:
<221> NAME/KEY: MOD_RES
<222> LOCATION: (30)..(30)
<223> OTHER INFORMATION: AMIDATION

<400> SEQUENCE: 29

Xaa Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 30
<211> LENGTH: 30
<212> TYPE: PRT
<213> ORGANISM: Artificial Sequence
<220> FEATURE:
<223> OTHER INFORMATION: GLP-1 Analogue
<220> FEATURE:
<221> NAME/KEY: MISC_FEATURE
<222> LOCATION: (1)..(1)
<223> OTHER INFORMATION: Xaa = phenylacetyl
<220> FEATURE:
<221> NAME/KEY: MOD_RES
<222> LOCATION: (30)..(30)
<223> OTHER INFORMATION: AMIDATION

<400> SEQUENCE: 30

Xaa Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 31
<211> LENGTH: 30
<212> TYPE: PRT
<213> ORGANISM: Artificial Sequence
<220> FEATURE:
<223> OTHER INFORMATION: GLP-1 Analogue
<220> FEATURE:
<221> NAME/KEY: MISC_FEATURE
<222> LOCATION: (1)..(1)
<223> OTHER INFORMATION: Xaa = 3-fluoro-4-hydroxyphenyl-acetyl
<220> FEATURE:
<221> NAME/KEY: MOD_RES
<222> LOCATION: (30)..(30)
<223> OTHER INFORMATION: AMIDATION

<400> SEQUENCE: 31

Xaa Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 32
<211> LENGTH: 30
<212> TYPE: PRT
<213> ORGANISM: Artificial Sequence
<220> FEATURE:
<223> OTHER INFORMATION: GLP-1 Analogue
<220> FEATURE:
<221> NAME/KEY: MISC_FEATURE
<222> LOCATION: (1)..(1)
<223> OTHER INFORMATION: Xaa = 4-imidazol-carbonyl
<220> FEATURE:
<221> NAME/KEY: MOD_RES
<222> LOCATION: (30)..(30)
<223> OTHER INFORMATION: AMIDATION

<400> SEQUENCE: 32
```

Xaa Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 33
<211> LENGTH: 30
<212> TYPE: PRT
<213> ORGANISM: Artificial Sequence
<220> FEATURE:
<223> OTHER INFORMATION: GLP-1 Analogue
<220> FEATURE:
<221> NAME/KEY: MMISC_FEATURE
<222> LOCATION: (1)..(1)
<223> OTHER INFORMATION: Xaa = 4-nitrophenyl-acetyl
<220> FEATURE:
<221> NAME/KEY: MOD_RES
<222> LOCATION: (30)..(30)
<223> OTHER INFORMATION: AMIDATION

<400> SEQUENCE: 33

Xaa Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 34
<211> LENGTH: 30
<212> TYPE: PRT
<213> ORGANISM: Artificial Sequence
<220> FEATURE:
<223> OTHER INFORMATION: GLP-1 Analogue
<220> FEATURE:
<221> NAME/KEY: MISC_FEATURE
<222> LOCATION: (1)..(1)
<223> OTHER INFORMATION: Xaa = 3-chloro-4-hydroxyphenyl-acetyl
<220> FEATURE:
<221> NAME/KEY: MOD_RES
<222> LOCATION: (30)..(30)
<223> OTHER INFORMATION: AMIDATION

<400> SEQUENCE: 34

Xaa Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 35
<211> LENGTH: 30
<212> TYPE: PRT
<213> ORGANISM: Artificial Sequence
<220> FEATURE:
<223> OTHER INFORMATION: GLP-1 Analogue
<220> FEATURE:
<221> NAME/KEY: MISC_FEATURE
<222> LOCATION: (1)..(1)
<223> OTHER INFORMATION: Xaa = 4-hydroxyphenylacetyl
<220> FEATURE:
<221> NAME/KEY: MOD_RES
<222> LOCATION: (30)..(30)
<223> OTHER INFORMATION: AMIDATION

<400> SEQUENCE: 35

Xaa Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

```
<210> SEQ ID NO 36
<211> LENGTH: 30
<212> TYPE: PRT
<213> ORGANISM: Artificial Sequence
<220> FEATURE:
<223> OTHER INFORMATION: GLP-1 Analogue
<220> FEATURE:
<221> NAME/KEY: MISC_FEATURE
<222> LOCATION: (1)..(1)
<223> OTHER INFORMATION: Xaa = 4-aminophenyl-acetyl
<220> FEATURE:
<221> NAME/KEY: MOD_RES
<222> LOCATION: (30)..(30)
<223> OTHER INFORMATION: AMIDATION

<400> SEQUENCE: 36

Xaa Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 37
<211> LENGTH: 30
<212> TYPE: PRT
<213> ORGANISM: Artificial Sequence
<220> FEATURE:
<223> OTHER INFORMATION: GLP-1 Analogue
<220> FEATURE:
<221> NAME/KEY: MISC_FEATURE
<222> LOCATION: (1)..(1)
<223> OTHER INFORMATION: Xaa = 3-(3-hydroxyphenyl)-propionyl
<220> FEATURE:
<221> NAME/KEY: MOD_RES
<222> LOCATION: (30)..(30)
<223> OTHER INFORMATION: AMIDATION

<400> SEQUENCE: 37

Xaa Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 38
<211> LENGTH: 30
<212> TYPE: PRT
<213> ORGANISM: Artificial Sequence
<220> FEATURE:
<223> OTHER INFORMATION: GLP-1 Analogue
<220> FEATURE:
<221> NAME/KEY: MISC_FEATURE
<222> LOCATION: (1)..(1)
<223> OTHER INFORMATION: Xaa = 3-phenyl-propionyl
<220> FEATURE:
<221> NAME/KEY: MOD_RES
<222> LOCATION: (30)..(30)
<223> OTHER INFORMATION: AMIDATION

<400> SEQUENCE: 38

Xaa Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 39
<211> LENGTH: 30
<212> TYPE: PRT
<213> ORGANISM: Artificial Sequence
<220> FEATURE:
<223> OTHER INFORMATION: GLP-1 Analogue
<220> FEATURE:
```

```
<221> NAME/KEY: MISC_FEATURE
<222> LOCATION: (1)..(1)
<223> OTHER INFORMATION: Xaa = 3-(4-aminophenyl)-propionyl
<220> FEATURE:
<221> NAME/KEY: MOD_RES
<222> LOCATION: (30)..(30)
<223> OTHER INFORMATION: AMIDATION

<400> SEQUENCE: 39

Xaa Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 40
<211> LENGTH: 30
<212> TYPE: PRT
<213> ORGANISM: Artificial Sequence
<220> FEATURE:
<223> OTHER INFORMATION: GLP-1 Analogue
<220> FEATURE:
<221> NAME/KEY: MISC_FEATURE
<222> LOCATION: (1)..(1)
<223> OTHER INFORMATION: Xaa = 3-(4-nitrophenyl)-propionyl
<220> FEATURE:
<221> NAME/KEY: MOD_RES
<222> LOCATION: (30)..(30)
<223> OTHER INFORMATION: AMIDATION

<400> SEQUENCE: 40

Xaa Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 41
<211> LENGTH: 30
<212> TYPE: PRT
<213> ORGANISM: Artificial Sequence
<220> FEATURE:
<223> OTHER INFORMATION: GLP-1 Analogue
<220> FEATURE:
<221> NAME/KEY: MISC_FEATURE
<222> LOCATION: (1)..(1)
<223> OTHER INFORMATION: Xaa = 3-(2-hydroxyphenyl)-propionyl
<220> FEATURE:
<221> NAME/KEY: MOD_RES
<222> LOCATION: (30)..(30)
<223> OTHER INFORMATION: AMIDATION

<400> SEQUENCE: 41

Xaa Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 42
<211> LENGTH: 30
<212> TYPE: PRT
<213> ORGANISM: Artificial Sequence
<220> FEATURE:
<223> OTHER INFORMATION: GLP-1 Analogue
<220> FEATURE:
<221> NAME/KEY: MISC_FEATURE
<222> LOCATION: (1)..(1)
<223> OTHER INFORMATION: Xaa =  3-(3,4-difluorophenyl)-propionyl
<220> FEATURE:
<221> NAME/KEY: MOD_RES
<222> LOCATION: (30)..(30)
<223> OTHER INFORMATION: AMIDATION
```

```
<400> SEQUENCE: 42

Xaa Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 43
<211> LENGTH: 30
<212> TYPE: PRT
<213> ORGANISM: Artificial Sequence
<220> FEATURE:
<223> OTHER INFORMATION: GLP-1 Analogue
<220> FEATURE:
<221> NAME/KEY: MISC_FEATURE
<222> LOCATION: (1)..(1)
<223> OTHER INFORMATION: Xaa = 3-(2,4-dihydroxyphenyl)-propionyl
<220> FEATURE:
<221> NAME/KEY: MOD_RES
<222> LOCATION: (30)..(30)
<223> OTHER INFORMATION: AMIDATION

<400> SEQUENCE: 43

Xaa Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30
```

ANALOGUES OF GLP-1

BACKGROUND OF THE INVENTION

This application is a United States national stage filing under 35 U.S.C. §371 of international (PCT) application No. PCT/US2004/042045, filed Dec. 15, 2004 and designating the US, which application claims priority to U.S. provisional application 60/529,822 filed Dec. 16, 2003.

The present invention is directed to peptide analogues of glucagon-like peptide-1, the pharmaceutically-acceptable salts thereof, to methods of using such analogues to treat mammals and to pharmaceutical compositions useful therefor comprising said analogues.

Glucagon-like peptide-1 (7-36) amide (GLP-1) is synthesized in the intestinal L-cells by tissue-specific post-translational processing of the glucagon precursor preproglucagon (Varndell, J. M., et al., J. Histochem Cytochem, 1985:33: 1080-6) and is released into the circulation in response to a meal. The plasma concentration of GLP-1 rises from a fasting level of approximately 15 pmol/L to a peak postprandial level of 40 pmol/L. It has been demonstrated that, for a given rise in plasma glucose concentration, the increase in plasma insulin is approximately threefold greater when glucose is administered orally compared with intravenously (Kreymann, B., et al., Lancet 1987:2, 1300-4). This alimentary enhancement of insulin release, known as the incretin effect, is primarily humoral and GLP-1 is now thought to be the most potent physiological incretin in humans. In addition to the insulinotropic effect, GLP-1 suppresses glucagon secretion, delays gastric emptying (Wettergren A., et al., Dig Dis Sci 1993:38: 665-73) and may enhance peripheral glucose disposal (D'Alessio, D. A. et al., J. Clin Invest 1994:93:2293-6).

In 1994, the therapeutic potential of GLP-1 was suggested following the observation that a single subcutaneous (s/c) dose of GLP-1 could completely normalize postprandial glucose levels in patients with non-insulin-dependent diabetes mellitus (NIDDM) (Gutniak, M. K., et al., Diabetes Care 1994:17:1039-44). This effect was thought to be mediated both by increased insulin release and by a reduction in glucagon secretion. Furthermore, an intravenous infusion of GLP-1 has been shown to delay postprandial gastric emptying in patients with NIDDM (Williams, B., et al., J. Clin Endo Metab 1996:81:327-32). Unlike sulphonylureas, the insulinotropic action of GLP-1 is dependent on plasma glucose concentration (Holz, G. G. 4$^{th}$, et al., Nature 1993:361:362-5). Thus, the loss of GLP-1-mediated insulin release at low plasma glucose concentration protects against severe hypoglycemia. This combination of actions gives GLP-1 unique potential therapeutic advantages over other agents currently used to treat NIDDM.

Numerous studies have shown that when given to healthy subjects, GLP-1 potently influences glycemic levels as well as insulin and glucagon concentrations (Orskov, C, Diabetologia 35:701-711, 1992; Hoist, J. J., et al., *Potential of GLP-1 in diabetes management* in Glucagon III, Handbook of Experimental Pharmacology, Lefevbre P J, Ed. Berlin, Springer Verlag, 1996, p. 311-326), effects which are glucose dependent (Kreymann, B., et al., Lancet ii:1300-1304, 1987; Weir, G. C., et al., Diabetes 38:338-342, 1989). Moreover, it is also effective in patients with diabetes (Gutniak, M., N. Engl J Med 226:1316-1322, 1992; Nathan, D. M., et al., Diabetes Care 15:270-276, 1992), normalizing blood glucose levels in type 2 diabetic subjects (Nauck, M. A., et al., Diagbetologia 36:741-744, 1993), and improving glycemic control in type 1 patients (Creutzfeldt, W. O., et al., Diabetes Care 19:580-586, 1996), raising the possibility of its use as a therapeutic agent.

GLP-1 is, however, metabolically unstable, having a plasma half-life ($t_{1/2}$) of only 1-2 min in vivo. Exogenously administered GLP-1 is also rapidly degraded (Deacon, C. F., et al., Diabetes 44:1126-1131, 1995). This metabolic instability limits the therapeutic potential of native GLP-1. Hence, there is a need for GLP-1 analogues that are more active and/or are more metabolically stable than native GLP-1.

SUMMARY OF THE INVENTION

In one aspect the invention features a compound according to formula (I), $$(R2R3)\text{-}A^7\text{-}A^8\text{-}A^9\text{-}A^{10}\text{-}A^{11}\text{-}A^{12}\text{-}A^{13}\text{-}A^{14}\text{-}A^{15}\text{-}A^{16}\text{-}$$
$$A^{17}\text{-}A^{18}\text{-}A^{19}\text{-}A^{20}\text{-}A^{21}\text{-}A^{22}\text{-}A^{23}\text{-}A^{24}\text{-}A^{25}\text{-}A^{26}\text{-}$$
$$A^{27}\text{-}A^{28}\text{-}A^{29}\text{-}A^{30}\text{-}A^{31}\text{-}A^{32}\text{-}A^{33}\text{-}A^{34}\text{-}A^{35}\text{-}A^{36}\text{-}$$
$$A^{37}\text{-}A^{38}\text{-}A^{39}\text{-}R^1, \qquad (I)$$

wherein $A^7$ is L-His, Ura, Paa, Pta, Amp, Tma-His, des-amino-His, or deleted;

$A^8$ is Ala, β-Ala, Gly, Ser, D-Ala, Aib, Acc, N-Me-Ala, N-Me-D-Ala or N-Me-Gly;

$A^9$ is Glu, N-Me-Glu, N-Me-Asp or Asp;

$A^{10}$ is Gly, Acc, β-Ala or Aib;

$A^{11}$ is Thr or Ser;

$A^{12}$ is Phe, Acc, Aic, Aib, 2-Pal, 3-Pal, 4-Pal, 1Nal, 2Nal, Cha, Trp or $(X^6,X^7,X^8,X^9,X^{10})$Phe;

$A^{13}$ is Thr or Ser;

$A^{14}$ is Ser or Aib;

$A^{15}$ is Asp or Glu;

$A^{16}$ is Val, Acc, Aib, Leu, Ile, Tle, Nle, Abu, Ala or Cha;

$A^{17}$ is Ser, Aib or Thr;

$A^{18}$ is Ser, Lys or Thr;

$A^{19}$ is Tyr, Cha, Phe, 2-Pal, 3-Pal, 4-Pal, 1Nal, 2Nal, Acc or $(X^6,X^7,X^8,X^9,X^{10})$Phe;

$A^{20}$ is Leu, Acc, Aib, Nle, Ile, Cha, Tle, Val, Phe or $(X^6,X^7,X^8,X^9,X^{10})$Phe;

$A^{21}$ is Glu or Asp;

$A^{22}$ is Gly, Acc, β-Ala, Glu or Aib;

$A^{23}$ is Gln, Asp, Asn or Glu;

$A^{24}$ is Ala, Aib, Val, Abu, Tle or Acc;

$A^{25}$ is Ala, Aib, Val, Abu, Tle, Acc, Lys, Arg, hArg, Orn, HN—CH$((CH_2)_n$—N$(R^{10}R^{11}))$—C(O) or HN—CH$((CH_2)_e$—X$^3)$—C(O);

$A^{26}$ is Lys, Arg, hArg, Orn, Lys(N$^\epsilon$-decanoyl)), HN—CH$((CH_2)_n$—N$(R^{10}R^{11}))$—C(O) or HN—CH$((CH_2)_e$—X$^3)$—C(O);

$A^{27}$ is Glu, Asp, Leu, Aib or Lys;

$A^{28}$ is Phe, 2-Pal, 3-Pal, 4-Pal, 1Nal, 2Nal, $(X^6,X^7,X^8,X^9,X^{10})$Phe, Aic, Acc, Aib, Cha or Trp;

$A^{29}$ is Ile, Acc, Aib, Leu, Nle, Cha, Tle, Val, Abu, Ala or Phe;

$A^{30}$ is Ala, Aib or Acc;

$A^{31}$ is Trp, 2-Pal, 3-Pal, 4-Pal, 1Nal, 2Nal, Phe, Acc, Aib, $(X^6,X^7,X^8,X^9,X^{10})$Phe or Cha;

$A^{32}$ is Leu, Acc, Aib, Nle, Ile, Cha, Tle, Phe, $(X^6,X^7,X^8,X^9,X^{10})$Phe or Ala;

$A^{33}$ is Val, Acc, Aib, Leu, Ile, Tle, Nle, Cha, Ala, Phe, Abu, Lys or $(X^6,X^7,X^8,X^9,X^{10})$Phe;

$A^{34}$ is Lys, Arg, hArg, Orn, HN—CH$((CH_2)_n$—N$(R^{10}R^{11}))$—C(O) or HN—CH$((CH_2)_e$—X$^3)$—C(O);

$A^{35}$ is β-Ala, D-Ala, Gaba, Ava, HN—$(CH_2)_m$—C(O), Aib, Acc, D-Arg or a D-amino acid;

$A^{36}$ is L- or D-Arg, D- or L-Lys, or Lys($N^\epsilon$-decanoyl) or Lys($N^\epsilon$-dodecanoyl) or D- or L-hArg, D- or L-Orn or HN—CH(($CH_2)_n$—N($R^{10}R^{11}$))—C(O), or HN—CH(($CH_2)_e$—$X^3$)—C(O);

$A^{37}$ is Gly, β-Ala, Gaba, Aib, Acc, Act, Apc, Aun, Ava, Pro, Dhp, Dmt, Pip, L- or D-Arg, L- or D-Asp or Glu, Lys($N^\epsilon$-decanoyl), Lys($N^\epsilon$-dodecanoyl), Lys($N^\epsilon$-octanoyl), Lys($N^\epsilon$-tetradecanoyl), or Ser(O-decanoyl);

$A^{38}$ is D- or L-His, L- or D-Ala, Asn, Gln, Ser, Thr, Acc, Ado, Aib, Apc, Act, Arg, Ava, Gly, β-Ala, Gaba, or HN—($CH_2)_s$—C(O);

$A^{39}$ is D- or L-His, L- or D-Ala, Asn, Gln, Ser, Thr, Acc, Ado, Aib, Apc, Act, Arg, Aun, Gly, β-Ala, Gaba, Lys($N^\epsilon$-octanoyl), HN—($CH_2)_s$—C(O), or deleted;

$R^1$ is OH, $NH_2$; ($C_1$-$C_{30}$)alkoxy, or NH—$X^2$—$CH_2$—$Z^0$, wherein $X^2$ is a ($C_0$-$C_2$), ($C_4$-$C_9$) or ($C_{11}$-$C_{19}$)hydrocarbon moiety and $Z^0$ is H, OH, $CO_2H$ or $CONH_2$;

$X^3$ is 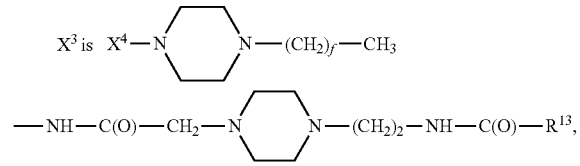

—NH—C(O)—$CH_2$—N⌬N—$(CH_2)_2$—NH—C(O)—$R^{13}$, or —C(O)—$NHR^{12}$, wherein $X^4$ is, independently for each occurrence, —C(O)—, —NH—C(O)— or —$CH_2$—, and wherein f is, independently for each occurrence, an integer from 1 to 29 inclusive;

each of $R^2$ and $R^3$ is independently selected from the group consisting of H, ($C_1$-$C_{30}$)alkyl, ($C_2$-$C_{30}$)alkenyl, optionally substituted phenyl($C_1$-$C_{30}$)alkyl, optionally substituted naphthyl($C_1$-$C_{30}$)alkyl, hydroxy($C_1$-$C_{30}$)alkyl, hydroxy($C_2$-$C_{30}$)alkenyl, hydroxyphenyl($C_1$-$C_{30}$)alkyl, and hydroxynaphthyl($C_1$-$C_{30}$)alkyl;

wherein the phenyl group of said optionally substituted phenyl($C_1$-$C_{30}$)alkyl moiety, and said naphthyl group of said optionally substituted naphthyl($C_1$-$C_{30}$)alkyl moiety each is, independently for each occurrence, substituted with 1 or more substituents selected, independently for each occurrence, from the group consisting of halo, OH, $NH_2$, $NO_2$ and CN; or one of $R^2$ and $R^3$ is

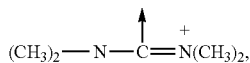

($C_1$-$C_{30}$)acyl, ($C_1$-$C_{30}$)alkylsulfonyl, C(O)$X^5$,

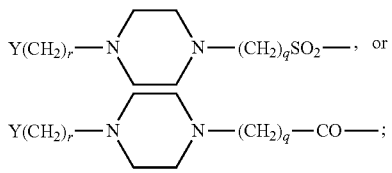

wherein Y is H, OH or $NH_2$; r is 0 to 4; q is 0 to 4; and $X^5$ is ($C_1$-$C_{30}$)alkyl, ($C_2$-$C_{30}$)alkenyl, phenyl($C_1$-$C_{30}$)alkyl, naphthyl($C_1$-$C_{30}$)alkyl, hydroxy($C_1$-$C_{30}$)alkyl, hydroxy($C_2$-$C_{30}$)alkenyl, hydroxyphenyl($C_1$-$C_{30}$)alkyl or hydroxynaphthyl($C_1$-$C_{30}$)alkyl;

$X^6, X^7, X^8, X^9, X^{10}$ for each occurrence is independently selected from the group consisting of H, ($C_1$-$C_6$)alkyl, OH, $OR^4$, $NO_2$, CN, and halo;

$R^4$ is ($C_1$-$C_{30}$)alkyl, ($C_2$-$C_{30}$)alkenyl, phenyl($C_1$-$C_{30}$)alkyl, naphthyl($C_1$-$C_{30}$)alkyl, hydroxy($C_1$-$C_{30}$)alkyl, hydroxy($C_2$-$C_{30}$)alkenyl, hydroxyphenyl($C_1$-$C_{30}$)alkyl or hydroxynaphthyl($C_1$-$C_{30}$)alkyl;

e is, independently for each occurrence, an integer from 1 to 4 inclusive;

m is, independently for each occurrence, an integer from 5 to 24 inclusive;

s is, independently for each occurrence, an integer from 5 to 10 or from 12 to 20 inclusive;

n is, independently for each occurrence, an integer from 1 to 5, inclusive;

each of $R^{10}$ and $R^{11}$ is, independently for each occurrence, H, ($C_1$-$C_{30}$)alkyl, ($C_1$-$C_{30}$)acyl, ($C_1$-$C_{30}$)alkylsulfonyl, —C((NH)($NH_2$)) or

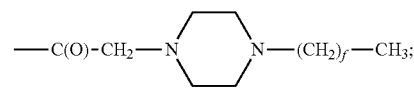

and $R^{12}$ and $R^{13}$ each is, independently for each occurrence, ($C_1$-$C_{30}$)alkyl;

provided that:

when $A^7$ is Ura, Paa or Pta, then $R^2$ and $R^3$ are deleted;

when $R^{10}$ is ($C_1$-$C_{30}$)acyl, ($C_1$-$C_{30}$)alkylsulfonyl, —C((NH)($NH_2$)) or

then $R^{11}$ is H or ($C_1$-$C_{30}$)alkyl;

(i) at least one amino acid of a compound of formula (I) is not the same as the native sequence of hGLP-1(7-38 or -39)$NH_2$ or hGLP-1(7-38 or -39)OH;

(ii) a compound of formula (I) is not an analogue of hGLP-1(7-38 or -39)$NH_2$ or hGLP-1(7-38, or -39)OH wherein a single position has been substituted by Ala;

(iii) a compound of formula (I) is not ($Arg^{26,34}$, $Lys^{38}$)hGLP-1(7-38)-E, ($Lys^{26}(N^\epsilon$-alkanoyl))hGLP-1(7-38)-E, ($Lys^{34}(N^\epsilon$-alkanoyl))hGLP-1(7-38)-E, ($Lys^{26,34}$-bis($N^\epsilon$-alkanoyl))hGLP-1(7-38)-E, ($Arg^{26}$, $Lys^{34}(N^\epsilon$-alkanoyl))hGLP-1(8-38)-E, ($Arg^{26,34}$, $Lys^{36}(N^\epsilon$-alkanoyl))hGLP-1(7-38)-E or ($Arg^{26,34}$, $Lys^{38}(N^\epsilon$-alkanoyl))hGLP-1(7-38)-E, wherein E is —OH or —$NH_2$;

(iv) a compound of formula (I) is not $Z^1$-hGLP-1(7-38)-OH, $Z^1$-hGLP-1(7-38)-$NH_2$; wherein $Z^1$ is selected from the group consisting of:

(a) ($Arg^{26}$), ($Arg^{34}$), ($Arg^{26,34}$), ($Lys^{36}$), ($Arg^{26}$, $Lys^{36}$), ($Arg^{34}$, $Lys^{36}$), (D-$Lys^{36}$), ($Arg^{36}$), (D-$Arg^{36}$), ($Arg^{26,34}$, $Lys^{36}$) or ($Arg^{26,36}$, $Lys^{34}$);

(b) ($Asp^{21}$);

(c) at least one of ($Aib^8$), (D-$Ala^8$) and ($Asp^9$); and (d) ($Tyr^7$), (N-acyl-$His^7$), (N-alkyl-$His^7$), (N-acyl-D-$His^7$) or (N-alkyl-D-$His^7$); and (v) a compound of formula (I) is not a combination of any two of the substitutions listed in groups (a) to (d); or a pharmaceutically acceptable salt thereof.

A preferred group of compounds of the immediately foregoing compound is where $A^{11}$ is Thr; $A^{13}$ is Thr; $A^{15}$ is Asp; $A^{17}$ is Ser; $A^{18}$ is Ser or Lys; $A^{21}$ is Glu; $A^{23}$ is Gln or Glu; $A^{27}$ is Glu, Leu, Aib or Lys; and $A^{31}$ is Trp, Phe, 1Nal or 2Nal; or a pharmaceutically acceptable salt thereof.

A preferred group of compounds of the immediately foregoing group of compounds is where $A^9$ is Glu, N-Me-Glu or N-Me-Asp; $A^{12}$ is Phe, Acc, 1Nal, 2Nal, or Aic; $A^{16}$ is Val, Acc or Aib; $A^{19}$ is Tyr, 1Nal or 2Nal; $A^{20}$ is Leu, Acc or Cha; $A^{24}$ is Ala, Aib or Acc; $A^{25}$ is Ala, Aib, Acc, Lys, Arg, hArg, Orn, HN—CH(($CH_2$)$_n$—N($R^{10}R^{11}$))—C(O) or HN—CH(($CH_2$)$_e$—$X^3$)—C(O); $A^{28}$ is Phe, 1Nal or 2Nal; $A^{29}$ is Ile or Acc; $A^{30}$ is Ala or Aib; $A^{32}$ is Leu, Acc or Cha; and $A^{33}$ is Val, Lys or Acc; or a pharmaceutically acceptable salt thereof.

A preferred group of compounds of the immediately foregoing group of compounds is where $A^8$ is Ala, Gly, Ser, D-Ala, Aib, A6c, A5c, N-Me-Ala, N-Me-D-Ala or N-Me-Gly; $A^{10}$ is Gly; $A^{12}$ is Phe, 1Nal, 2Nal, A6c or A5c; $A^{16}$ is Val, A6c or A5c; $A^{20}$ is Leu, A6c, A5c or Cha; $A^{22}$ is Gly, β-Ala, Glu or Aib; $A^{24}$ is Ala or Aib; $A^{29}$ is Ile, A6c or A5c; $A^{32}$ is Leu, A6c, A5c or Cha; $A^{33}$ is Val, Lys, A6c or A5c; $A^{35}$ is Aib, β-Ala, Ado, A6c, A5c, D-Arg or Acc; $A^{37}$ is Gly, Aib, β-Ala, D-Ala, Pro, Asp, Aun or D-Asp; $A^{38}$ is D- or L-His, Asn, Ser, Apc, Act, Gly, β-Ala or Gaba; and $A^{39}$ is Ser, Thr or Aib; or a pharmaceutically acceptable salt thereof.

A preferred group of compounds of the immediately foregoing group of compounds is where $X^4$ for each occurrence is —C(O)—; and $R^1$ is OH or $NH_2$; or a pharmaceutically acceptable salt thereof.

A preferred group of compounds of the immediately foregoing group of compounds or a pharmaceutically acceptable salt thereof is where $R^2$ is H and $R^3$ is ($C_1$-$C_{30}$)alkyl, ($C_2$-$C_{30}$)alkenyl, ($C_1$-$C_{30}$)acyl, ($C_1$-$C_{30}$)alkylsulfonyl, $$\text{HO}-(CH_2)_2-N\diagup\diagdown N-(CH_2)_2SO_2-,$$

$$\text{HO}-(CH_2)_2-N\diagup\diagdown N-CH_2-CO- \text{ or}$$

$$H_2N-(CH_2)_2-N\diagup\diagdown N-CH_2-CO-.$$

A preferred group of the compounds of the immediately foregoing group of compounds or a pharmaceutically acceptable salt thereof, is where $R^{10}$ is ($C_1$-$C_{30}$)acyl, ($C_1$-$C_{30}$)alkylsulfonyl or $$-C(O)-CH_2-N\diagup\diagdown N-(CH_2)_f-CH_3, \text{ and } R^{11} \text{ is H.}$$

A preferred group of the compounds of the immediately foregoing group of compounds or a pharmaceutically acceptable salt thereof, is where $R^{10}$ is ($C_4$-$C_{20}$)acyl, ($C_4$-$C_{20}$)alkylsulfonyl or $$-C(O)-CH_2-N\diagup\diagdown N-(CH_2)_f-CH_3.$$

A preferred compound of the formula (I) is where $A^8$ is Ala, D-Ala, Aib, A6c, A5c, N-Me-Ala, N-Me-D-Ala or N-Me-Gly; $A^{10}$ is Gly; $A^{12}$ is Phe, 1Nal, 2Nal, A6c or A5c; $A^{16}$ is Val, A6c or A5c; $A^{20}$ is Leu, A6c, A5c or Cha; $A^{22}$ is Gly, β-Ala, Glu or Aib; $A^{24}$ is Ala or Aib; $A^{29}$ is Ile, A6c or A5c; $A^{32}$ is Leu, A6c, A5c or Cha; $A^{33}$ is Val, Lys, A6c or A5c; $A^{35}$ is Aib, β-Ala, Ado, A6c, A5c or D-Arg; and $A^{37}$ is Gly, Aib, β-Ala, D-Ala, Pro or D-Asp; $A^{38}$ is D- or L-His, Asn, Ser, Gly, β-Ala or Gaba; and $A^{39}$ is Ser, or deleted; $X^4$ for each occurrence is —C(O)—; e for each occurrence is independently 1 or 2; $R^1$ is OH or $NH_2$; $R^{10}$ is ($C_1$-$C_{30}$)acyl, ($C_1$-$C_{30}$)alkylsulfonyl or $$-C(O)-CH_2-N\diagup\diagdown N-(CH_2)_f-CH_3,$$

and $R^{11}$ is H; or a pharmaceutically acceptable salt thereof.

More preferred of the immediately foregoing compounds is where $R^{10}$ is ($C_4$-$C_{20}$)acyl, ($C_4$-$C_{20}$)alkylsulfonyl or $$-C(O)-CH_2-N\diagup\diagdown N-(CH_2)_f-CH_3,$$

or a pharmaceutically acceptable salt thereof.

A more preferred compound of formula (I) is where said compound is the pharmaceutically acceptable salt thereof.

More preferred of the immediately foregoing group of compounds is a compound of the formula:

($Aib^{8,35}$, $Arg^{26,34}$, $Phe^{31}$, $Pro^{37}$, $Ser^{38,39}$)hGLP-1(7-39)-$NH_2$; (SEQ ID NO:1)

($Aib^{8,35,37}$, $Arg^{26,34}$, $Phe^{31}$, $Asn^{38}$)hGLP-1(7-38)-$NH_2$; (SEQ ID NO:2)

($Aib^{8,35,37}$, $Arg^{26,34}$, $Phe^{31}$, $Ser^{38}$)hGLP-1(7-38) $NH_2$; (SEQ ID NO:3)

($Aib^{8,35,37}$, $Gaba^{38}$)hGLP-1(7-38) $NH_2$; (SEQ ID NO:4)

($Aib^{8,35,37}$, $Arg^{26,34}$, $Phe^{31}$, $His^{38}$)hGLP-1(7-38) $NH_2$; (SEQ ID NO:5)

($Aib^{8,35}$, $Arg^{26,34}$, $Phe^{31}$, β-$Ala^{37}$, $His^{38}$)hGLP-1(7-38) $NH_2$; (SEQ ID NO:6)

($Aib^{8,35,37}$, $Arg^{26,34}$, D-$His^{38}$)hGLP-1(7-38) $NH_2$; (SEQ ID NO:7)

($Aib^{8,35,37}$, β-$Ala^{38}$)hGLP-1(7-38) $NH_2$; (SEQ ID NO:8)

($Aib^{8,35}$, $Arg^{26,34}$, β-$Ala^{37}$, $His^{38}$)hGLP-1(7-38) $NH_2$; (SEQ ID NO:9)

($Aib^{8,35,37}$, $Arg^{26,34}$, $Phe^{31}$, $Gly^{38}$)hGLP-1(7-38) $NH_2$; (SEQ ID NO:10)

($Aib^{8,35,37}$, $Arg^{26,34}$, $Gly^{38}$)hGLP-1(7-38) $NH_2$; (SEQ ID NO:11)

($Aib^{8,35,37}$, $Arg^{26,34}$, β-$Ala^{38}$)hGLP-1(7-38) $NH_2$; (SEQ ID NO:12)

($Aib^{8,35,37}$, $Arg^{26,34}$, $Gaba^{38}$)hGLP-1(7-38) $NH_2$; (SEQ ID NO:13)

($Aib^{8,35,37}$, $Arg^{34}$, $Phe^{31}$, $His^{38}$)hGLP-1(7-38) $NH_2$; (SEQ ID NO:14)

(Aib⁸,³⁵,³⁷, Arg²⁶,³⁴, His³⁸)hGLP-1(7-38) NH₂; (SEQ ID NO:15)
(Aib⁸,³⁵,³⁷, Arg²⁶,³⁴, Phe³¹, Gaba³⁸)hGLP-1(7-38) NH₂; (SEQ ID NO:16)
(Aib⁸,³⁵,³⁷, Arg²⁶,³⁴, Phe³¹, Ava³⁸)hGLP-1(7-38) NH₂; (SEQ ID NO:17)
(Aib⁸,³⁵,³⁷, Arg²⁶,³⁴, Ava³⁸)hGLP-1(7-38) NH₂; (SEQ ID NO:18)
(Aib⁸,³⁵,³⁷, Arg³⁴, Phe³¹, D-His³⁸)hGLP-1(7-38) NH₂; (SEQ ID NO:19)
(Aib⁸,³⁵,³⁷, Arg³⁴, Phe³¹, Gly³⁸)hGLP-1(7-38) NH₂; (SEQ ID NO:20)
(Aib⁸,³⁵,³⁷, Gly³⁸)hGLP-1(7-38) NH₂; (SEQ ID NO:21)
(Aib⁸,³⁵,³⁷, Arg²⁶,³⁴, Phe³¹, D-His³⁸)hGLP-1(7-38) NH₂; (SEQ ID NO:22)
(Aib⁸,³⁵, Arg²⁶,³⁴, Phe³¹, β-Ala³⁷, D-His³⁸)hGLP-1(7-38) NH₂; (SEQ ID NO:23)
(Aib⁸,³⁵,³⁷, Arg²⁶,³⁴, Phe³¹, β-Ala³⁸)hGLP-1(7-38) NH₂; (SEQ ID NO:24)
(Aib⁸,³⁵, Arg²⁶,³⁴, Phe³¹, β-Ala³⁷,³⁸)hGLP-1(7-38) NH₂; (SEQ ID NO:25)
(Aib⁸,³⁵,³⁷, Arg³⁴, Phe³¹, β-Ala³⁸)hGLP-1(7-38) NH₂; (SEQ ID NO:26) or
(Aib⁸,³⁵,³⁷, Arg³⁴, Phe³¹, Gaba³⁸)hGLP-1(7-38) NH₂; (SEQ ID NO:27)
or a pharmaceutically acceptable salt thereof.

In another aspect, the present invention is directed to a compound according to formula (II), $$R^7\text{-}A^8\text{-}A^9\text{-}A^{10}\text{-}A^{11}\text{-}A^{12}\text{-}A^{13}\text{-}A^{14}\text{-}A^{15}\text{-}A^{16}\text{-}A^{17}\text{-}A^{18}\text{-}\\A^{19}\text{-}A^{20}\text{-}A^{21}\text{-}A^{22}\text{-}A^{23}\text{-}A^{24}\text{-}A^{25}\text{-}A^{26}\text{-}A^{27}\text{-}A^{28}\text{-}\\A^{29}\text{-}A^{30}\text{-}A^{31}\text{-}A^{32}\text{-}A^{33}\text{-}A^{34}\text{-}A^{35}\text{-}A^{36}\text{-}A^{37}\text{-}A^{38}\text{-}\\A^{39}\text{-}R^1, \quad (II)$$

wherein $R^7$ is

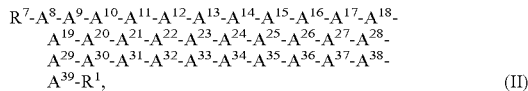

$A^8$ is Ala, β-Ala, Gly, Ser, D-Ala, Aib, Acc, N-Me-Ala, N-Me-D-Ala or N-Me-Gly;
$A^9$ is Glu, N-Me-Glu, N-Me-Asp or Asp;
$A^{10}$ is Gly, Acc, β-Ala or Aib;
$A^{11}$ is Thr or Ser;
$A^{12}$ is Phe, Acc, Aic, Aib, 2-Pal, 3-Pal, 4-Pal, 1Nal, 2Nal, Cha, Trp or $(X^6,X^7,X^8,X^9,X^{10})$Phe;
$A^{13}$ is Thr or Ser;
$A^{14}$ is Ser or Aib;
$A^{15}$ is Asp or Glu;
$A^{16}$ is Val, Acc, Aib, Leu, Ile, Tle, Nle, Abu, Ala or Cha;
$A^{17}$ is Ser, Aib or Thr;
$A^{18}$ is Ser, Lys or Thr;
$A^{19}$ is Tyr, Cha, Phe, 2-Pal, 3-Pal, 4-Pal, 1Nal, 2Nal, Acc or $(X^6,X^7,X^8,X^9,X^{10})$Phe;
$A^{20}$ is Leu, Acc, Aib, Nle, Ile, Cha, Tle, Val, Phe or $(X^6,X^7,X^8,X^9,X^{10})$Phe;
$A^{21}$ is Glu or Asp;
$A^{22}$ is Gly, Acc, β-Ala, Glu or Aib;
$A^{23}$ is Gln, Asp, Asn or Glu;
$A^{24}$ is Ala, Aib, Val, Abu, Tle or Acc;
$A^{25}$ is Ala, Aib, Val, Abu, Tle, Acc, Lys, Arg, hArg, Orn, HN—CH((CH₂)ₙ—N(R¹⁰R¹¹))—C(O) or HN—CH((CH₂)ₑ—X³)—C(O);
$A^{26}$ is Lys, Arg, hArg, Orn, Lys(Nᵉ-decanoyl)), HN—CH((CH₂)ₙ—N(R¹⁰R¹¹))—C(O) or HN—CH((CH₂)ₑ—X³)—C(O);
$A^{27}$ is Glu Asp, Leu, Aib or Lys;
$A^{28}$ is Phe, 2-Pal, 3-Pal, 4-Pal, 1Nal, 2Nal, $(X^6,X^7,X^8,X^9,X^{10})$Phe, Aic, Acc, Aib, Cha or Trp;
$A^{29}$ is Ile, Acc, Aib, Leu, Nle, Cha, Tle, Val, Abu, Ala or Phe;
$A^{30}$ is Ala, Aib or Acc;
$A^{31}$ is Trp, 2-Pal, 3-Pal, 4-Pal, 1Nal, 2Nal, Phe, Acc, Aib, $(X^6,X^7,X^8,X^9,X^{10})$Phe or Cha;
$A^{32}$ is Leu, Acc, Aib, Nle, Ile, Cha, Tle, Phe, $(X^6,X^7,X^8,X^9,X^{10})$Phe or Ala;
$A^{33}$ is Val, Acc, Aib, Leu, Ile, Tle, Nle, Cha, Ala, Phe, Abu, Lys or $(X^6,X^7,X^8,X^9,X^{10})$Phe;
$A^{34}$ is Lys, Arg, hArg, Orn, HN—CH((CH₂)ₙ—N(R¹⁰R¹¹))—C(O) or HN—CH((CH₂)ₑ—X³)—C(O);
$A^{35}$ is β-Ala, D-Ala, Gaba, Ava, HN—(CH₂)ₘ—C(O), Aib, Acc, D-Arg, a D-amino acid or deleted;
$A^{36}$ is L- or D-Arg, D- or L-Lys, or Lys(Nᵉ-decanoyl) or Lys(Nᵉ-dodecanoyl) or D- or L-hArg, D- or L-Orn or HN—CH((CH₂)ₙ—N(R¹⁰R¹¹))—C(O), HN—CH((CH₂)ₑ—X³)—C(O), or deleted;
$A^{37}$ is Gly, β-Ala, Gaba, Aib, Acc, Act, Apc, Aun, Ava, Pro, Dhp, Dmt, Pip, L- or D-Arg, L- or D-Asp or Glu, Lys(Nᵉ-decanoyl), Lys(Nᵉ-dodecanoyl), Lys(Nᵉ-octanoyl), Lys(Nᵉ-tetradecanoyl), Ser(O-decanoyl), or deleted;
$A^{38}$ is D- or L-His, L- or D-Ala, Asn, Gln, Ser, Thr, Acc, Ado, Aib, Apc, Act, Arg, Ava, Gly, β-Ala, Gaba, HN—(CH₂)ₘ—C(O), or deleted;
$A^{39}$ is D- or L-His, L- or D-Ala, Asn, Gln, Ser, Thr, Acc, Ado, Aib, Apc, Act, Arg, Aun, Gly, β-Ala, Gaba, Lys(Nᵉ-octanoyl), HN—(CH₂)ₘ—C(O), or deleted;
$R^1$ is OH, NH₂; $(C_1\text{-}C_{30})$alkoxy, or NH—X²—CH₂—Z⁰, wherein X² is a $(C_0\text{-}C_{20})$hydrocarbon moiety and Z⁰ is H, OH, CO₂H or CONH₂;

$X^3$ is

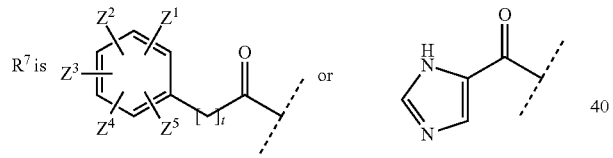

or —C(O)—NHR¹², wherein X⁴ is, independently for each occurrence, —C(O)—, —NH—C(O)— or —CH₂—, and wherein f is, independently for each occurrence, an integer from 1 to 29 inclusive;
$X^6,X^7,X^8,X^9,X^{10}$ for each occurrence is independently selected from the group consisting of H, $(C_1\text{-}C_6)$alkyl, OH, OR⁴, NO₂, CN, and halo;
$R^4$ is $(C_1\text{-}C_{30})$alkyl, $(C_2\text{-}C_{30})$alkenyl, phenyl$(C_1\text{-}C_{30})$alkyl, naphthyl$(C_1\text{-}C_{30})$alkyl, hydroxy$(C_1\text{-}C_{30})$alkyl, hydroxy$(C_2\text{-}C_{30})$alkenyl, hydroxyphenyl$(C_1\text{-}C_{30})$alkyl or hydroxynaphthyl$(C_1\text{-}C_{30})$alkyl;
$Z^1,Z^2,Z^3,Z^4,Z^5$ for each occurrence is independently selected from the group consisting of H, $(C_1\text{-}C_6)$alkyl, OH, OR⁴, NO₂, CN, and halo; $Z^1$ and $Z^2$ can join together to form a ring system;
e is, independently for each occurrence, an integer from 1 to 4 inclusive;
m is, independently for each occurrence, an integer from 5 to 24 inclusive;
n is, independently for each occurrence, an integer from 1 to 5, inclusive;

t is, independently for each occurrence, an integer from 0 to 4, inclusive;

each of $R^{10}$ and $R^{11}$ is, independently for each occurrence, H, $(C_1-C_{30})$alkyl, $(C_1-C_{30})$acyl, $(C_1-C_{30})$alkylsulfonyl, —C((NH)(NH$_2$)) or

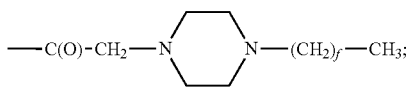

and $R^{12}$ and $R^{13}$ each is, independently for each occurrence, $(C_1-C_{30})$alkyl;

provided that:

$R^7$ is not C(O)$X^{11}$, wherein $X^{11}$ is phenyl$(C_1-C_{30})$alkyl, naphthyl$(C_1-C_{30})$alkyl, hydroxy$(C_1-C_{30})$alkyl, hydroxy$(C_2-C_{30})$alkenyl, hydroxyphenyl$(C_1-C_{30})$alkyl or hydroxynaphthyl$(C_1-C_{30})$alkyl;

when $R^{10}$ is $(C_1-C_{30})$acyl, $(C_1-C_{30})$alkylsulfonyl, —C((NH)(NH$_2$)) or

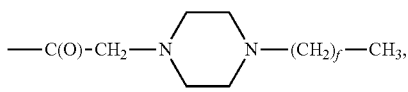

then $R^{11}$ is H or $(C_1-C_{30})$alkyl;

or a pharmaceutically acceptable salt thereof.

A preferred group of compounds of the immediately foregoing compound is where $A^{11}$ is Thr; $A^{13}$ is Thr; $A^{15}$ is Asp; $A^{17}$ is Ser; $A^{18}$ is Ser or Lys; $A^{21}$ is Glu; $A^{23}$ is Gln or Glu; $A^{27}$ is Glu, Leu, Aib or Lys; and $A^{31}$ is Trp, Phe, 1Nal or 2Nal; or a pharmaceutically acceptable salt thereof.

A preferred group of compounds of the immediately foregoing group of compounds is where $A^7$ is 4-imidazol-carbonyl, 4-nitrophenyl-acetyl, 3-chloro-4-hydroxyphenyl-acetyl, 4-hydroxyphenyl-acetyl, 3-(4-aminophenyl)-propionyl, 3-(4-nitrophenyl)-propionyl, 3-(3,4-difluorophenyl)-propionyl, 3-fluoro-4-hydroxyphenyl-acetyl or 4-aminophenyl-acetyl; $A^9$ is Glu, N-Me-Glu or N-Me-Asp; $A^{12}$ is Phe, Acc, 1Nal, 2Nal or Aic; $A^{16}$ is Val, Acc or Aib; $A^{19}$ is Tyr, 1Nal or 2Nal; $A^{20}$ is Leu, Acc or Cha; $A^{24}$ is Ala, Aib or Acc; $A^{25}$ is Ala, Aib, Acc, Lys, Arg, hArg, Orn, HN—CH((CH$_2$)$_n$—N($R^{10}R^{11}$))—C(O) or HN—CH((CH$_2$)$_e$—$X^3$)—C(O); $A^{28}$ is Phe, 1Nal or 2Nal; $A^{29}$ is Ile or Acc; $A^{30}$ is Ala or Aib; $A^{32}$ is Leu, Acc or Cha; and $A^{33}$ is Val, Lys or Acc; or a pharmaceutically acceptable salt thereof.

A preferred group of compounds of the immediately foregoing group of compounds is where $A^8$ is Ala, Gly, Ser, D-Ala, Aib, A6c, A5c, N-Me-Ala, N-Me-D-Ala or N-Me-Gly; $A^{10}$ is Gly; $A^{12}$ is Phe, 1Nal, 2Nal, A6c or A5c; $A^{16}$ is Val, A6c or A5c; $A^{20}$ is Leu, A6c, A5c or Cha; $A^{22}$ is Gly, β-Ala, Glu or Aib; $A^{24}$ is Ala or Aib; $A^{29}$ is Ile, A6c or A5c; $A^{32}$ is Leu, A6c, A5c or Cha; $A^{33}$ is Val, Lys, A6c or A5c; $A^{35}$ is Aib, β-Ala, Ado, A6c, A5c, D-Arg, Acc or Gly; $A^{37}$ is Gly, Aib, β-Ala, D-Ala, Pro, Asp, Aun or D-Asp; $A^{38}$ is D- or L-His, Asn, Ser, Apc, Act, Gly, β-Ala or Gaba; and $A^{39}$ is Ser, Thr or Aib; or a pharmaceutically acceptable salt thereof.

A preferred group of compounds of the immediately foregoing group of compounds is where $X^4$ for each occurrence is —C(O)—; and $R^1$ is OH or NH$_2$; or a pharmaceutically acceptable salt thereof.

A preferred compound of the formula (II) is where $A^8$ is Ala, D-Ala, Aib, A6c, A5c, N-Me-Ala, N-Me-D-Ala or N-Me-Gly; $A^{10}$ is Gly; $A^{12}$ is Phe, 1Nal, 2Nal, A6c or A5c; $A^{16}$ is Val, A6c or A5c; $A^{20}$ is Leu, A6c, A5c or Cha; $A^{22}$ is Gly, β-Ala, Glu or Aib; $A^{24}$ is Ala or Aib; $A^{29}$ is Ile, A6c or A5c; $A^{32}$ is Leu, A6c, A5c or Cha; $A^{33}$ is Val, Lys, A6c or A5c; $A^{35}$ is Aib, β-Ala, Ado, A6c, A5c D-Arg or Gly; and $A^{37}$ is Gly, Aib, β-Ala, D-Ala, Pro or D-Asp; $A^{38}$ is D- or L-His, Asn, Ser, Gly, β-Ala or Gaba; and $A^{39}$ is Ser, or deleted; $X^4$ for each occurrence is —C(O)—; e for each occurrence is independently 1 or 2; $R^1$ is OH or NH$_2$; $R^{10}$ is $(C_1-C_{30})$acyl, $(C_1-C_{30})$alkylsulfonyl or

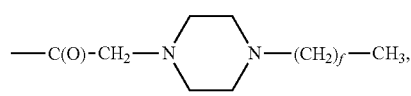

and $R^{11}$ is H; or a pharmaceutically acceptable salt thereof.

More preferred of the immediately foregoing compounds is where $R^{10}$ is $(C_4-C_{20})$acyl, $(C_4-C_{20})$alkylsulfonyl or

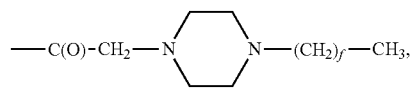

or a pharmaceutically acceptable salt thereof.

A more preferred compound of formula (II) is where said compound is of the formula:

(4Hppa$^7$)GLP-1(7-36)NH$_2$; (SEQ ID NO:28)
(3Hppa$^7$)GLP-1(7-36)NH$_2$; (SEQ ID NO:29)
(phenylacetyl$^7$)hGLP-1(7-36)NH$_2$; (SEQ ID NO:30)
((3-fluoro-4-hydroxyphenyl-acetyl)$^7$)hGLP-1(7-36)NH$_2$; (SEQ ID NO:31)
((4-imidazol-carbonyl)$^7$)hGLP-1(7-36) NH$_2$; (SEQ ID NO:32)
((4-nitrophenyl-acetyl)$^7$)hGLP-1(7-36) NH$_2$; (SEQ ID NO:33)
((3-chloro-4-hydroxyphenyl-acetyl)$^7$)hGLP-1(7-36) NH$_2$; (SEQ ID NO:34)
((4-hydroxyphenylacetyl)$^7$)hGLP-1(7-36) NH$_2$; (SEQ ID NO:35)
((4-aminophenyl-acetyl)$^7$)hGLP-1(7-36) NH$_2$; (SEQ ID NO:36)
((3-(3-hydroxyphenyl)-propionyl)$^7$)hGLP-1(7-36) NH$_2$; (SEQ ID NO:37)
((3-phenyl-propionyl)$^7$)hGLP-1(7-36) NH$_2$; (SEQ ID NO:38)
((3-(4-aminophenyl)-propionyl)$^7$)hGLP-1(7-36) NH$_2$; (SEQ ID NO:39)
((3-(4-nitrophenyl)-propionyl)$^7$)hGLP-1(7-36) NH$_2$; (SEQ ID NO:40)
((3-(2-hydroxyphenyl)-propionyl)$^7$)hGLP-1(7-36) NH$_2$; (SEQ ID NO:41)
((3-(3,4-difluorophenyl)-propionyl)$^7$)hGLP-1(7-36) NH$_2$; (SEQ ID NO:42) or
((3-(2,4-dihydroxyphenyl)-propionyl)$^7$)hGLP-1(7-36) NH$_2$; (SEQ ID NO:43)

or a pharmaceutically acceptable salt thereof.

A more preferred compound of formula (II) is where said compound is the pharmaceutically acceptable salt thereof.

Another more preferred compound of formula (I) or (II) is each of the compounds that are specifically enumerated hereinbelow in the Examples section of the present disclosure, or a pharmaceutically acceptable salt thereof.

In another aspect, the present invention provides a pharmaceutical composition comprising an effective amount of a compound of formula (I) or (II) as defined hereinabove or a pharmaceutically acceptable salt thereof and a pharmaceutically acceptable carrier or diluent.

In yet another aspect, the present invention provides a method of eliciting an agonist effect from a GLP-1 receptor in a subject in need thereof which comprises administering to said subject an effective amount of a compound of formula (I) or (II) as defined hereinabove or a pharmaceutically acceptable salt thereof.

In a further aspect, the present invention provides a method of treating a disease selected from the group consisting of Type I diabetes, Type II diabetes, obesity, glucagonomas, secretory disorders of the airway, metabolic disorder, arthritis, osteoporosis, central nervous system disease, restenosis, neurodegenerative disease, renal failure, congestive heart failure, nephrotic syndrome, cirrhosis, pulmonary edema, hypertension, treatment of respiratory distress (U.S. Patent Application Publication No. 2004/0235726 A1) and disorders wherein the reduction of food intake is desired, in a subject in need thereof which comprises administering to said subject an effective amount of a compound of formula (I) or (II) as defined hereinabove or a pharmaceutically acceptable salt thereof. A preferred method of the immediately foregoing method is where the disease being treated is Type I diabetes or Type II diabetes. GLP-1 analogues of the present invention that elicit an antagonist effect from a subject can be used for treating the following: hypoglycemia and malabsorption syndrome associated with gastroectomy or small bowel resection.

With the exception of the N-terminal amino acid, all abbreviations (e.g. Ala) of amino acids in this disclosure stand for the structure of —NH—CH(R)—CO—, wherein R and R' each is, independently, hydrogen or the side chain of an amino acid (e.g., R=CH$_3$ and R'=H for Ala) or R and R' may be joined to form a ring system. For the N-terminal amino acid, the abbreviation stands for the structure of =N—C(R)(R')—CO—, wherein "=" represents the bonds to R$^2$ and R$^3$, defined herein. R$^2$ and R$^3$ are as defined above, except when A$^7$ is Ura, Paa or Pta, in which case R$^2$ and R$^3$ are not present since Ura, Paa and Pta are considered here as des-amino amino acids.

The application employs the following commonly understood abbreviations:

| | |
|---|---|
| Abu | α-aminobutyric acid |
| Acc | 1-amino-1-cyclo(C$_3$—C$_9$)alkyl carboxylic acid |
| A3c | 1-amino-1-cyclopropanecarboxylic acid |
| A4c | 1-amino-1-cyclobutanecarboxylic acid |
| A5c | 1-amino-1-cyclopentanecarboxylic acid |
| A6c | 1-amino-1-cyclohexanecarboxylic acid |
| Act | 4-amino-4-carboxytetrahydropyran |
| Ado | 12-aminododecanoic acid |
| Aec | 4-(2-aminoethyl)-1-carboxymethyl-piperazine |

(i.e., the structure: 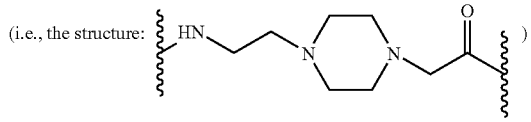 )

| | |
|---|---|
| Aib | α-aminoisobutyric acid |
| Aic | 2-aminoindan-2-carboxylic acid |
| Ala or A | alanine |
| β-Ala | beta-alanine |
| Amp | 4-amino-phenylalanine; |
| Apc | 4-amino-4-carboxypiperidine: |
| Arg or R | arginine |
| hArg | homoarginine |
| Asn or N | asparagine |
| Asp or D | aspartic acid |
| Aun | 11-aminoundecanoic acid |
| Ava | 5-aminovaleric acid |
| Cha | β-cyclohexylalanine |
| Dhp | 3,4-dehydroproline |
| Dmt | 5,5-dimethylthiazolidine-4-carboxylic acid |
| Gaba | γ-aminobutyric acid |
| Gln or Q | glutamine |
| Glu or E | glutamic acid |
| Gly or G | glycine |
| His or H | histidine |
| 4Hppa | 3-(4-hydroxyphenyl)propionic acid |
| 3Hppa | 3-(3-hydroxyphenyl)propionic acid |
| 3Hyp | trans-3-hydroxy-L-proline |
| | (i.e., (2S, 3S)-3-hydroxypyrrolidine-2-carboxylic acid) |
| 4Hyp | 4-hydroxyproline |
| | (i.e., (2S, 4R)-4-hydroxypyrrolidine-2-carboxylic acid) |
| Ile or I | isoleucine |
| Leu or L | leucine |
| Lys or K | lysine |
| 1Nal | β-(1-naphthyl)alanine |
| 2Nal | β-(2-naphthyl)alanine |

| | |
|---|---|
| Nle | norleucine |
| N-Me-Ala | N-methyl-alanine; |
| N-Me-Asp | N-methyl-aspartic acid |
| N-Me-Glu | N-methyl-glutamic acid; |
| N-Me-Gly | N-methyl-glycine; |
| Nva | norvaline |
| Orn | ornithine |
| Paa | trans-3-(3-pyridyl) acrylic acid; |
| 2Pal | β-(2-pyridinyl)alanine |
| 3Pal | β-(3-pyridinyl)alanine |
| 4Pal | β-(4-pyridinyl)alanine |
| Phe or F | phenylalanine |
| (3,4,5F)Phe | 3,4,5-trifluorophenylalanine |
| (2,3,4,5,6)Phe | 2,3,4,5,6-pentafluorophenylalanine |
| Pip | pipecolic acid |
| Pro or P | proline |
| Pta | (4-pyridylthio) acetic acid; |
| Ser or S | serine |
| Thr or T | threonine |
| Tle | tert-leucine |
| Tma-His | N,N-tetramethylamidino-histidine; |
| Trp or W | tryptophan |
| Tyr or Y | tyrosine |
| Ura | urocanic acid. |
| Val or V | valine |

Certain other abbreviations used herein are defined as follows:

| | |
|---|---|
| 2BrZ | 2-bromobenzyloxycarbonyl |
| 2ClZ | 2-chlorobenzyloxycarbonyl |
| Boc: | tert-butyloxycarbonyl |
| Bzl: | benzyl |
| DCM: | dichloromethane |
| DIC: | N,N-diisopropylcarbodiimide |
| DIEA: | diisopropylethyl amine |
| Dmab: | 4-{N-(1-(4,4-dimethyl-2,6-dioxocyclohexylidene)-3-methylbutyl)-amino} benzyl |
| DMAP: | 4-(dimethylamino)pyridine |
| DMF | dimethylformamide |
| DNP: | 2,4-dinitrophenyl |
| Fm | formyl |
| Fmoc: | 9-Fluorenylmethyloxycarbonyl |
| HBTU: | 2-(1H-benzotriazole-1-yl)-1,1,3,3-tetramethyluronium hexafluorophosphate |
| cHex | cyclohexyl |
| HF | hydrogen fluoride, |
| HOAT: | O-(7-azabenzotriazol-1-yl)-1,1,3,3-tetramethyluronium hexafluorophosphate |
| HOBt: | 1-hydroxy-benzotriazole |
| Mmt: | 4-methoxytrityl |
| NMP: | N-methylpyrrolidone |
| OcHex | O-cyclohexyl |
| PAM resin | 4-hydroxymethylphenylacetamidomethyl resin |
| Pbf: | 2,2,4,6,7-pentamethyldihydrobenzofuran-5-sulfonyl |
| tBu: | tert-butyl |
| TIS: | triisopropylsilane |
| TOS: | tosyl |
| trt | trityl |
| TFA: | trifluoro acetic acid |
| TFFH: | tetramethylfluoroforamidinium hexafluorophosphate |
| Xan | xanthyl |
| Z: | benzyloxycarbonyl |

In the above formula, hydroxyalkyl, hydroxyphenylalkyl, and hydroxynaphthylalkyl may contain 1-4 hydroxy substituents. $COX^5$ stands for $-C=O\cdot X^5$. Examples of $-C=O\cdot X^5$ include, but are not limited to, acetyl and phenylpropionyl.

What is meant by Lys($N^\epsilon$-alkanoyl) is represented by the following structure:

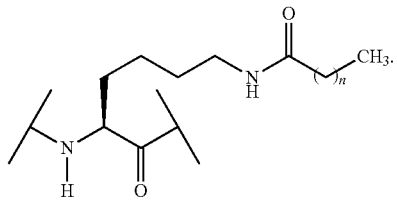

What is meant by Lys($N^\epsilon$-alkylsulfonyl) is represented by the following structure:

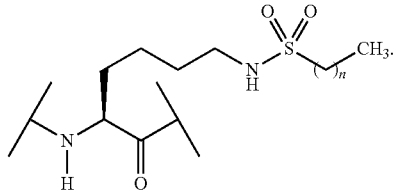

What is meant by Lys($N^\epsilon$-(2-(4-alkyl-1-piperazine)acetyl)) is represented by the following structure:

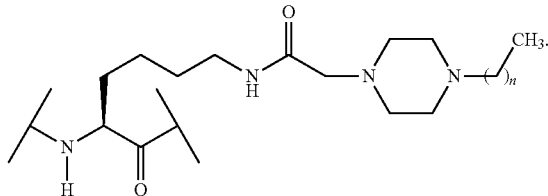

What is meant by Asp(1-(4-alkyl-piperazine)) is represented by the following structure:

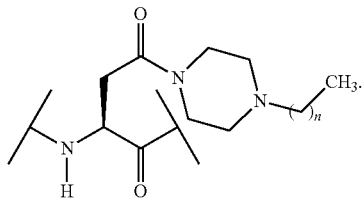

What is meant by Asp(1-alkylamino) is represented by the following structure:

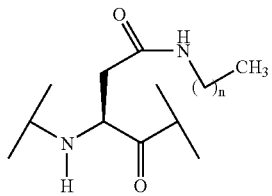

What is meant by Lys(N$^\epsilon$-Aec-alkanoyl) is represented by the structure:

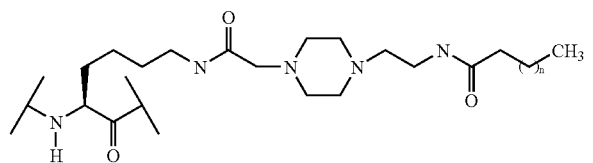

The variable n in the foregoing structures is 1-30. Lys(N$^\epsilon$-Aec-alkanoyl) is represented by the structure:

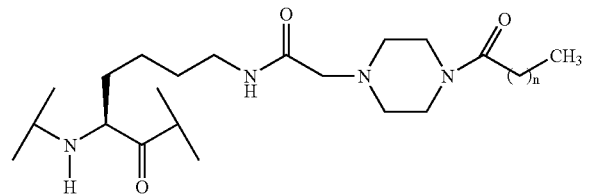

The term "halo" encompasses fluoro, chloro, bromo and iodo.

The term "$(C_1-C_{30})$hydrocarbon moiety" encompasses alkyl, alkenyl and alkynyl, and in the case of alkenyl and alkynyl there are $C_2-C_{30}$.

A peptide of this invention is also denoted herein by another format, e.g., (A5c$^8$)hGLP-1(7-36)NH$_2$; with the substituted amino acids from the natural sequence placed between the first set of parentheses (e.g., A5c$^8$ for Ala$^8$ in hGLP-1). The abbreviation GLP-1 means glucagon-like peptide-1; hGLP-1 means human glucagon-like peptide-1. The numbers between the parentheses refer to the number of amino acids present in the peptide (e.g., hGLP-1(7-36) is amino acids 7 through 36 of the peptide sequence for human GLP-1). The sequence for hGLP-1(7-37) is listed in Mojsov, S., Int. J. Peptide Protein Res,. 40, 1992, pp. 333-342. The designation "NH$_2$" in hGLP-1(7-36)NH$_2$ indicates that the C-terminus of the peptide is amidated. hGLP-1(7-36) means that the C-terminus is the free acid. In hGLP-1(7-38), residues in positions 37 and 38 are Gly and Arg, respectively.

DETAILED DESCRIPTION

The peptides of this invention can be prepared by standard solid phase peptide synthesis. See, e.g., Stewart, J. M., et al., Solid Phase Synthesis (Pierce Chemical Co., 2d ed. 1984). The substituents R$^2$ and R$^3$ of the above generic formula may be attached to the free amine of the N-terminal amino acid by standard methods known in the art. For example, alkyl groups, e.g., $(C_1-C_{30})$alkyl, may be attached using reductive alkylation. Hydroxyalkyl groups, e.g., $(C_1-C_{30})$hydroxyalkyl, may also be attached using reductive alkylation wherein the free hydroxy group is protected with a t-butyl ester. Acyl groups, e.g., COE$^1$, may be attached by coupling the free acid, e.g., E$^1$COOH, to the free amine of the N-terminal amino acid by mixing the completed resin with 3 molar equivalents of both the free acid and diisopropylcarbodiimide in methylene chloride for one hour. If the free acid contains a free hydroxy group, e.g., 3-fluoro-4-hydroxyphenylacetic acid, then the coupling should be performed with an additional 3 molar equivalents of HOBT.

When R$^1$ is NH—X$^2$—CH$_2$—CONH$_2$; (i.e., Z$^0$=CONH$_2$), the synthesis of the peptide starts with BocHN—X$^2$—CH$_2$—COOH which is coupled to the MBHA resin. If R$^1$ is NH—X$^2$—CH$_2$—COOH, (i.e., Z$^0$=COOH) the synthesis of the peptide starts with Boc-HN—X$^2$—CH$_2$—COOH which is coupled to PAM resin. For this particular step, 4 molar equivalents of Boc-HN—X$^2$—COOH, HBTU and HOBt and 10 molar equivalents of DIEA are used. The coupling time is about 8 hours.

In the synthesis of a GLP-1 analogue of this invention containing A5c, A6c, and/or Aib, the coupling time is 2 hrs for these residues and the residue immediately following them.

The substituents R$^2$ and R$^3$ of the above generic formula can be attached to the free amine of the N-terminal amino acid by standard methods known in the art. For example, alkyl groups, e.g., $(C_1-C_{30})$alkyl, can be attached using reductive alkylation. Hydroxyalkyl groups, e.g., $(C_1-C_{30})$hydroxyalkyl, can also be attached using reductive alkylation wherein the free hydroxy group is protected with a t-butyl ester. Acyl groups, e.g., COX$^5$, can be attached by coupling the free acid, e.g., X$^5$COOH, to the free amine of the N-terminal amino acid by mixing the completed resin with 3 molar equivalents of both the free acid and diisopropylcarbodiimide in methylene chloride for about one hour. If the free acid contains a free hydroxy group, e.g., 3-fluoro-4-hydroxyphenylacetic acid, then the coupling should be performed with an additional 3 molar equivalents of HOBT.

The peptides of this invention can be provided in the form of pharmaceutically acceptable salts. Examples of such salts include, but are not limited to, those formed with organic acids (e.g., acetic, lactic, maleic, citric, malic, ascorbic, succinic, benzoic, methanesulfonic, toluenesulfonic, or pamoic acid), inorganic acids (e.g., hydrochloric acid, sulfuric acid, or phosphoric acid), and polymeric acids (e.g., tannic acid, carboxymethyl cellulose, polylactic, polyglycolic, or copolymers of polylactic-glycolic acids). A typical method of making a salt of a peptide of the present invention is well known in the art and can be accomplished by standard methods of salt exchange. Accordingly, the TFA salt of a peptide of the present invention (the TFA salt results from the purification of the peptide by using preparative HPLC, eluting with TFA containing buffer solutions) can be converted into another salt, such as an acetate salt by dissolving the peptide in a small amount of 0.25 N acetic acid aqueous solution. The resulting solution is applied to a semi-prep HPLC column (Zorbax, 300 SB, C-8). The column is eluted with (1) 0.1N ammonium acetate aqueous solution for 0.5 hrs, (2) 0.25N acetic acid aqueous solution for 0.5 hrs and (3) a linear gradient (20% to 100% of solution B over 30 min) at a flow rate of 4 ml/min (solution A is 0.25N acetic acid aqueous solution; solution B is 0.25N acetic acid in acetonitrile/water, 80:20). The fractions containing the peptide are collected and lyophilized to dryness.

As is well known to those skilled in the art, the known and potential uses of GLP-1 is varied and multitudinous (See, Todd, J. F., et al., Clinical Science, 1998, 95, pp. 325-329; and Todd, J. F. et al., European Journal of Clinical Investigation, 1997, 27, pp.533-536). Thus, the administration of the compounds of this invention for purposes of eliciting an agonist effect can have the same effects and uses as GLP-1 itself. These varied uses of GLP-1 may be summarized as follows, treatment of: Type I diabetes, Type II diabetes, obesity, glucagonomas, secretory disorders of the airway, metabolic disorder, arthritis, osteoporosis, central nervous system diseases, restenosis, neurodegenerative diseases, renal failure, congestive heart failure, nephrotic syndrome, cirrhosis, pulmonary edema, hypertension, treatment of respiratory distress (U.S. Patent Application Publication No. 2004/0235726 A1), and disorders wherein the reduction of food intake is desired. GLP-1 analogues of the present invention that elicit an antagonist effect from a subject can be used for treating the following: hypoglycemia and malabsorption syndrome associated with gastroectomy or small bowel resection.

Accordingly, the present invention includes within its scope pharmaceutical compositions comprising, as an active ingredient, at least one of the compounds of formula (I) or (II) in association with a pharmaceutically acceptable carrier.

The dosage of active ingredient in the compositions of this invention may be varied; however, it is necessary that the amount of the active ingredient be such that a suitable dosage form is obtained. The selected dosage depends upon the desired therapeutic effect, on the route of administration, and on the duration of the treatment. In general, an effective dosage for the activities of this invention is in the range of $1 \times 10^{-7}$ to 200 mg/kg/day, preferably $1 \times 10^{-4}$ to 100 mg/kg/day, which can be administered as a single dose or divided into multiple doses.

The compounds of this invention can be administered by oral, parenteral (e.g., intramuscular, intraperitoneal, intravenous or subcutaneous injection, or implant), nasal, vaginal, rectal, sublingual or topical routes of administration and can be formulated with pharmaceutically acceptable carriers to provide dosage forms appropriate for each route of administration.

Solid dosage forms for oral administration include capsules, tablets, pills, powders and granules. In such solid dosage forms, the active compound is admixed with at least one inert pharmaceutically acceptable carrier such as sucrose, lactose, or starch. Such dosage forms can also comprise, as is normal practice, additional substances other than such inert diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration include, without limitation, pharmaceutically acceptable emulsions, solutions, suspensions, syrups, elixirs, and the like, containing inert diluents commonly used in the art, such as water. Besides such inert diluents, compositions can also include adjuvants, such as wetting agents, emulsifying and suspending agents, and sweetening, flavoring and perfuming agents.

Preparations according to this invention for parenteral administration include, without limitation, sterile aqueous or non-aqueous solutions, suspensions, emulsions, and the like. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteria-retaining filter, by incorporating sterilizing agents into the compositions, by irradiating the compositions, or by heating the compositions. They can also be manufactured in the form of sterile solid compositions which can be dissolved in sterile water, or some other sterile injectable medium immediately before use.

Compositions for rectal or vaginal administration are preferably suppositories which may contain, in addition to the active substance, excipients such as coca butter or a suppository wax.

Compositions for nasal or sublingual administration are also prepared with standard excipients well known in the art.

Further, a compound of this invention can be administered in a sustained release composition such as those described in the following patents and patent applications. U.S. Pat. No. 5,672,659 teaches sustained release compositions comprising a bioactive agent and a polyester. U.S. Pat. No. 5,595,760 teaches sustained release compositions comprising a bioactive agent in a gelable form. U.S. Pat. No. 5,821,221, teaches polymeric sustained release compositions comprising a bioactive agent and chitosan. U.S. Pat. No.5,916,883 teaches sustained release compositions comprising a bioactive agent and cyclodextrin. PCT Publication WO99/38536 teaches absorbable sustained release compositions of a bioactive agent. PCT Publication WO00/04916 teaches a process for making microparticles comprising a therapeutic agent such as a peptide in an oil-in-water process. PCT Publication WO00/09166 teaches complexes comprising a therapeutic agent such as a peptide and a phosphorylated polymer. PCT Publication WO00/25826 teaches complexes comprising a therapeutic agent such as a peptide and a polymer bearing a non-polymerizable lactone.

Unless defined otherwise, all technical and scientific terms used herein have the same meaning as commonly understood by one of ordinary skill in the art to which this invention belongs. Also, all publications, patent applications, patents and other references mentioned herein are hereby incorporated by reference, each in its entirety.

The following examples describe synthetic methods for making a peptide of this invention, which methods are well-known to those skilled in the art. Other methods are also known to those skilled in the art. The examples are provided for the purpose of illustration and are not meant to limit the scope of the present invention in any manner.

Boc-βAla-OH, Boc-D-Arg(Tos)-OH and Boc-D-Asp (OcHex) were purchased from Nova Biochem, San Diego, Calif. Boc-Aun-OH was purchased from Bachem, King of Prussia, Pa. Boc-Ava-OH and Boc-Ado-OH were purchased from Chem-Impex International, Wood Dale, Ill. Boc-Nal-OH was purchased from Synthetech, Inc. Albany, Oreg.

EXAMPLE 1

((3-fluoro-4-hydroxyphenyl-acetyl)$^7$)hGLP-1(7-36) NH$_2$(SEQ ID NO:31)

The title peptide, also referred to herein as ((3F, 4HO)-phenylacetyl$^7$)hGLP-1(7-36)NH$_2$; was synthesized on an Applied Biosystems model 433A peptide synthesizer (Foster City, Calif.) using Fluorenylmethyloxycarbonyl (Fmoc) chemistry. A Rink Amide-4-methylbenzylhydrylamine (MBHA) resin (Novabiochem., San Diego, Calif.) with substitution of 0.66 mmol/g was used. The Fmoc amino acids (AnaSpec, San Jose, Calif.) used were Fmoc-Ala-OH, Fmoc-Arg(Pbf)-OH, Fmoc-Asp(tBu)-OH, Fmoc-Gln(Trt)-OH, Fmoc-Glu(tBu)-OH, Fmoc-Gly-OH Fmoc-Ile-OH, Fmoc-Leu-OH, Fmoc-Lys(Boc)-OH, Fmoc-Phe-OH, Fmoc-Ser(tBu)-OH, Fmco-Tyr(tBu)-OH, Fmoc-Thr(tBu)-OH, Fmoc-Trp(Boc)-OH, and Fmoc-Val-OH. The last residue coupled to the resin was 3-Fluoro-4-hydroxyphenylacetic acid (Aldrich, Milwaukee, Wis.). The synthesis was carried out on a 0.1 mmol scale. The Fmoc groups were removed by treatment with 20% piperidine in N-methylpyrrolidone (NMP) for 30 min. In each coupling step, the Fmoc amino acid (3 eq, 0.3 mmol) was first pre-activated in 2 ml solution of 0.45 M 2-(1-H-benzotriazole-1-yl)-1,1,2,3-tetramethyluronium hexafluorophosphate/1-hydroxy-benzotriazole (HBTU/HOBT) in NMP. This activated amino acid ester, 1 ml of diisopropylethylamine (DIEA) and 1 ml of NMP were added to the resin. The ABI 433A peptide synthesizer was programmed to perform the following reaction cycle: (1) washing with NMP, (2) removing Fmoc protecting group with 20% piperidine in NMP for 30 min, (3) washing with NMP, (4) coupling with pre-activated Fmoc amino acid for 1 h. The resin was coupled successively according to the sequence of the title peptide. After the peptide chain was assembled the resin was washed completely by using N,N-dimethylformamide (DMF) and dichloromethane (DCM).

At the end of the assembly of the peptide chain, the peptide-resin was transferred to a reaction vessel on a shaker and treated with a mixture of TFA, H$_2$O and triisopropylsilane (TIS) (9.5 ml/0.85 ml/0.8 ml) for 4 h. The resin was filtered off and the filtrate was poured into 200 ml of ether. The precipitate was collected by filtration and washed thoroughly with ether. This crude product was dissolved in a mixture of acetonitrile and aqueous acetic acid solution and purified on a reverse-phase preparative HPLC system with a column (4×43 cm) of C$_{18}$ DYNAMAX-100 A$^0$ (Varian, Walnut Creek, Calif.). The column was eluted over approximately 1 hour using a linear gradient of 90% A:10% B to 50% A:50% B, where A was 0.1% TFA in water and B was 0.1% TFA in acetonitrile. The fractions were checked by analytical HPLC and those containing pure product were pooled and lyophilized to dryness to give 5.6 mg (1.7% yield) of a white solid. Purity was checked by using an analytical HPLC system and found to be 95.1%. Electro-spray ionization mass spectrometry (ESI-MS) analysis gave the molecular weight at 3312.3 (in agreement with the calculated molecular weight of 3312.6).

EXAMPLE 2

(Aib$^{8,35}$, Arg$^{26,34}$, Phe$^{31}$, Pro$^{37}$, Ser$^{38,39}$)hGLP-1(7-39)-NH$_2$(SEQ ID NO:1)

The title compound was synthesized substantially according to the procedure described for Example 1 using the appropriate protected amino acids (AnaSpec, San Jose, Calif.). At the end of the assembly of the protected peptide chain, an additional step was added to remove the N-terminal Fmoc-protecting group by using 20% piperidine in NMP for 30 min. The peptide resin was then washed, cleaved, purified and characterized using the procedures described for Example 1. Yield was 7.9%. Purity was 95.0%. Electro-spray ionization mass spectrometry (ESI-MS) analysis gave the molecular weight at 3629.40 (in agreement with the calculated molecular weight of 3628.00).

The following examples can be made according to the appropriate procedures described hereinabove:

Example 3 (Aib$^{8,35,37}$, Arg$^{26,34}$, Phe$^{31}$, Asn$^{38}$)hGLP-1(7-38)-NH$_2$(SEQ ID NO:2)

Example 4 ((4-imidazol-carbonyl)$^7$)hGLP-1(7-36)NH$_2$(SEQ ID NO:32)

Example 5 ((3-(3-hydroxyphenyl)-propionyl)$^7$)hGLP-1(7-36)NH$_2$(SEQ ID NO:37)

Example 6 ((3-phenyl-propionyl)$^7$)hGLP-1(7-36)NH$_2$(SEQ ID NO:38)

Example 7 ((4-nitrophenyl-acetyl)$^7$)hGLP-1(7-36)NH$_2$(SEQ ID NO:33)

Example 8 ((3-chloro-4-hydroxyphenyl-acetyl)$^7$)hGLP-1(7-36)NH$_2$(SEQ ID NO:34)

Example 9 ((4-hydroxyphenylacetyl)$^7$)hGLP-1(7-36)NH$_2$ (SEQ ID NO:35)

Example 10 (Aib$^{8,35,37}$, Arg$^{26,34}$, Phe$^{31}$, Ser$^{38}$)hGLP-1(7-38)NH$_2$(SEQ ID NO:3)

Example 11 (Aib$^{8,35,37}$, Gaba$^{38}$)hGLP-1(7-38)NH$_2$(SEQ ID NO:4)

Example 12 (Aib$^{8,35,37}$, Arg$^{26,34}$, Phe$^{31}$, His$^{38}$)hGLP-1(7-38)NH$_2$(SEQ ID NO:5)

Example 13 (Aib$^{8,35}$, Arg$^{26,34}$, Phe$^{31}$, β-Ala$^{37}$, His$^{38}$)hGLP-1(7-38)NH$_2$(SEQ ID NO:6)

Example 14 (Aib$^{8,35,37}$, Arg$^{26,34}$, D-His$^{38}$)hGLP-1(7-38)NH2 (SEQ ID NO:7)

Example 15 (Aib$^{8,35,37}$, β-Ala$^{38}$)hGLP-1(7-38)NH2 (SEQ ID NO:8)

Example 16 ((3-(4-aminophenyl)-propionyl)$^7$)hGLP-1(7-36)NH$_2$ (SEQ ID NO:39)

Example 17 ((3-(4-nitrophenyl)-propionyl)$^7$)hGLP-1(7-36)NH$_2$ (SEQ ID NO:40)

Example 18 ((3-(2-hydroxyphenyl)-propionyl)$^7$)hGLP-1(7-36)NH$_2$ (SEQ ID NO:41)

Example 19 ((3-(3,4-difluorophenyl)-propionyl)$^7$)hGLP-1(7-36)NH$_2$ (SEQ ID NO:42)

Example 20 (Aib$^{8,35}$, Arg$^{26,34}$, β-Ala$^{37}$, His$^{38}$)hGLP-1(7-38)NH$_2$ (SEQ ID NO:9)

Example 21 (Aib$^{8,35,37}$, Arg$^{26,34}$, Phe$^{31}$, Gly$^{38}$)hGLP-1(7-38)NH$_2$ (SEQ ID NO:10)

Example 22 (Aib$^{8,35,37}$, Arg$^{26,34}$, Gly$^{38}$)hGLP-1(7-38)NH$_2$ (SEQ ID NO:11)

Example 23 (Aib$^{8,35,37}$, Arg$^{26,34}$, β-Ala$^{38}$)hGLP-1(7-38)NH$_2$ (SEQ ID NO:12)

Example 24 (Aib$^{8,35,37}$, Arg$^{26,34}$, Gaba$^{38}$)hGLP-1(7-38)NH$_2$ (SEQ ID NO:13)

Example 25 (Aib$^{8,35,37}$, Arg$^{34}$, Phe$^{31}$, His$^{38}$)hGLP-1(7-38)NH$_2$ (SEQ ID NO:14)

Example 26 (Aib$^{8,35,37}$, Arg$^{26,34}$, His$^{38}$)hGLP-1(7-38)NH$_2$ (SEQ ID NO:15)
Example 27 (Aib$^{8,35,37}$, Arg$^{26,34}$, Phe$^{31}$, Gaba$^{38}$)hGLP-1(7-38)NH$_2$ (SEQ ID NO:16)
Example 28 (Aib$^{8,35,37}$, Arg$^{26,34}$, Phe$^{31}$, Ava$^{38}$)hGLP-1(7-38)NH$_2$ (SEQ ID NO:17)
Example 29 (Aib$^{8,35,37}$, Arg$^{26,34}$, Ava$^{38}$)hGLP-1(7-38)NH$_2$ (SEQ ID NO:18)
Example 30 (Aib$^{8,35,37}$, Arg$^{34}$, Phe$^{31}$, D-His$^{38}$)hGLP-1(7-38)NH$_2$ (SEQ ID NO:19)
Example 31 (Aib$^{8,35,37}$, Arg$^{34}$, Phe$^{31}$, Gly$^{38}$)hGLP-1(7-38)NH$_2$ (SEQ ID NO:20)
Example 32 ((4-aminophenyl-acetyl)$^7$)hGLP-1(7-36)NH$_2$ (SEQ ID NO:36)
Example 33 (Aib$^{8,35,37}$, Gly$^{38}$)hGLP-1(7-38)NH$_2$ (SEQ ID NO:21)
Example 34 (Aib$^{8,35,37}$, Arg$^{26,34}$, Phe$^{31}$, D-His$^{38}$)hGLP-1(7-38)NH$_2$ (SEQ ID NO:22)
Example 35 (Aib$^{8,35}$, Arg$^{26,34}$, Phe$^{31}$, β-Ala$^{37}$, D-His$^{38}$)hGLP-1(7-38)NH$_2$ (SEQ ID NO:23)
Example 36 (Aib$^{8,35,37}$, Arg$^{26,34}$, Phe$^{31}$, β-Ala$^{38}$)hGLP-1(7-38)NH$_2$ (SEQ ID NO:24)
Example 37 (Aib$^{8,35}$, Arg$^{26,34}$, Phe$^{31}$, β-Ala$^{37,38}$)hGLP-1(7-38)NH$_2$ (SEQ ID NO:25)
Example 38 (Aib$^{8,35,37}$, Arg$^{34}$, Phe$^{31}$, β-Ala$^{38}$)hGLP-1(7-38)NH$_2$ (SEQ ID NO:26)
Example 39 (Aib$^{8,35,37}$, Arg$^{34}$, Phe$^{31}$, Gaba$^{38}$)hGLP-1(7-38)NH$_2$ (SEQ ID NO:27)
Example 40 ((3-(2,4-dihydroxyphenyl)-propionyl)$^7$)hGLP-1(7-36)NH$_2$ (SEQ ID NO:43)

Physical data for a representative sampling of the compounds exemplified herein are given in Table 1.

TABLE 1

| Example Number | Molecular Weight Calculated | Molecular Weight MS(ES) | Purity (%) (HPLC) |
|---|---|---|---|
| 1 | 3312.60 | 3312.30 | 95.1 |
| 2 | 3628.00 | 3629.40 | 95.0 |
| 3 | 3555.94 | 3556.50 | 99.0 |
| 4 | 3254.59 | 3254.50 | 97.0 |
| 5 | 3308.68 | 3309.60 | 99.0 |
| 6 | 3292.68 | 3392.50 | 99.0 |
| 7 | 3323.65 | 3323.60 | 96.0 |
| 8 | 3329.10 | 3329.00 | 97.2 |
| 9 | 3294.65 | 3294.50 | 99.0 |
| 10 | 3528.91 | 3532.9 | 97.5 |
| 11 | 3509.95 | 3509.33 | 97.7 |
| 12 | 3578.98 | 3579.20 | 99.9 |
| 13 | 3564.95 | 3565.05 | 99.9 |
| 14 | 3618.01 | 3618.20 | 99.9 |
| 15 | 3495.92 | 3495.60 | 99.9 |
| 16 | 3307.69 | 3307.90 | 99.0 |
| 17 | 3337.68 | 3337.40 | 97.0 |
| 18 | 3308.68 | 3308.60 | 98.0 |
| 19 | 3328.66 | 3328.50 | 97.0 |
| 20 | 3603.99 | 3603.86 | 99.3 |
| 21 | 3498.89 | 3499.29 | 99.9 |

TABLE 1-continued

| Example Number | Molecular Weight Calculated | Molecular Weight MS(ES) | Purity (%) (HPLC) |
|---|---|---|---|
| 22 | 3537.92 | 3538.19 | 97.4 |
| 23 | 3551.95 | 3552.80 | 99.9 |
| 24 | 3565.98 | 3565.62 | 99.9 |
| 25 | 3550.96 | 3550.90 | 99.9 |
| 26 | 3618.01 | 3618.00 | 97.0 |
| 27 | 3526.94 | 3527.20 | 99.9 |
| 28 | 3540.97 | 3540.30 | 99.1 |
| 29 | 3580.01 | 3579.94 | 96.7 |
| 30 | 3550.96 | 3550.89 | 99.9 |
| 31 | 3470.87 | 3471.16 | 99.9 |
| 32 | 3293.67 | 3293.80 | 99.0 |
| 33 | 3481.90 | 3481.80 | 95.8 |
| 34 | 3578.90 | 3578.70 | 98.6 |
| 35 | 3564.95 | 3564.30 | 99.9 |
| 36 | 3512.91 | 3512.54 | 99.9 |
| 37 | 3498.89 | 3498.95 | 99.9 |
| 38 | 3484.90 | 3484.75 | 99.9 |
| 39 | 3498.93 | 3498.87 | 96.8 |
| 40 | 3324.68 | 3324.38 | 98.6 |

A compound of the present invention can be tested for activity as a GLP-1 binding compound according to the following procedure.

Cell Culture:

RIN 5F rat insulinoma cells (ATCC-# CRL-2058, American Type Culture Collection, Manassas, Va.), expressing the GLP-1 receptor, were cultured in Dulbecco's modified Eagle's medium (DMEM) containing 10% fetal calf serum, and maintained at about 37° C. in a humidifed atmosphere of 5% $CO_2$/95% air.

Radioligand Binding:

Membranes were prepared for radioligand binding studies by homogenization of the RIN cells in 20 ml of ice-cold 50 mM Tris-HCl with a Brinkman Polytron (Westbury, N.Y.) (setting 6, 15 sec). The homogenates were washed twice by centrifugation (39,000 g/10 min), and the final pellets were resuspended in 50 mM Tris-HCl, containing 2.5 mM $MgCl_2$, 0.1 mg/ml bacitracin (Sigma Chemical, St. Louis, Mo.), and 0.1% BSA. For assay, aliquots (0.4 ml) were incubated with 0.05 nM ($^{125}$I)GLP-1(7-36) (~2200 Ci/mmol, New England Nuclear, Boston, Mass.), with and without 0.05 ml of unlabeled competing test peptides. After a 100 min incubation (25° C.), the bound ($^{125}$I)GLP-1(7-36) was separated from the free by rapid filtration through GF/C filters (Brandel, Gaithersburg, Md.), which had been previously soaked in 0.5% polyethyleneimine. The filters were then washed three times with 5 ml aliquots of ice-cold 50 mM Tris-HCl, and the bound radioactivity trapped on the filters was counted by gamma spectrometry (Wallac LKB, Gaithersburg, Md.). Specific binding was defined as the total ($^{125}$I)GLP-1(7-36) bound minus that bound in the presence of 1000 nM GLP1(7-36) (Bachem, Torrence, Calif.).

What is claimed is:

1. A compound according to the formula:
   - (Aib$^{8,35}$, Arg$^{26,34}$, Phe$^{31}$, Pro$^{37}$, Ser$^{38,39}$)hGLP-1(7-39)-NH$_2$; (SEQ ID NO:1)
   - (Aib$^{8,35,37}$, Arg$^{26,34}$, Phe$^{31}$, Asn$^{38}$)hGLP-1(7-38)-NH$_2$; (SEQ ID NO:2)
   - (Aib$^{8,35,37}$, Arg$^{26,34}$, Phe$^{31}$, Ser$^{38}$)hGLP-1(7-38) NH$_2$; (SEQ ID NO:3)
   - (Aib$^{8,35,37}$, Gaba$^{38}$)hGLP-1(7-38) NH$_2$; (SEQ ID NO:4)
   - (Aib$^{8,35,37}$, Arg$^{26,34}$, Phe$^{31}$, His$^{38}$)hGLP-1(7-38) NH$_2$; (SEQ ID NO:5)
   - (Aib$^{8,35}$, Arg$^{26,34}$, Phe$^{31}$, β-Ala$^{37}$, His$^{38}$)hGLP-1(7-38) NH$_2$; (SEQ ID NO:6)
   - (Aib$^{8,35,37}$, Arg$^{26,34}$, D-His$^{38}$)hGLP-1(7-38) NH$_2$; (SEQ ID NO:7)
   - (Aib$^{8,35,37}$, β-Ala$^{38}$)hGLP-1(7-38) NH$_2$; (SEQ ID NO:8)
   - (Aib$^{8,35}$, Arg$^{26,34}$, β-Ala$^{37}$, His$^{38}$)hGLP-1(7-38) NH$_2$; (SEQ ID NO:9)
   - (Aib$^{8,35,37}$, Arg$^{26,34}$, Phe$^{31}$, Gly$^{38}$)hGLP-1(7-38) NH$_2$; (SEQ ID NO:10)
   - (Aib$^{8,35,37}$, Arg$^{26,34}$, Gly$^{38}$)hGLP-1(7-38) NH$_2$; (SEQ ID NO:11)
   - (Aib$^{8,35,37}$, Arg$^{26,34}$, β-Ala$^{38}$)hGLP-1(7-38) NH$_2$; (SEQ ID NO:12)
   - (Aib$^{8,35,37}$, Arg$^{26,34}$, Gaba$^{38}$)hGLP-1(7-38) NH$_2$; (SEQ ID NO:13)
   - (Aib$^{8,35,37}$, Arg$^{34}$, Phe$^{31}$, His$^{38}$)hGLP-1(7-38) NH$_2$; (SEQ ID NO:14)
   - (Aib$^{8,35,37}$, Arg$^{26,34}$, His$^{38}$)hGLP-1(7-38) NH$_2$; (SEQ ID NO:15)
   - (Aib$^{8,35,37}$, Arg$^{26,34}$, Phe$^{31}$, Gaba$^{38}$)hGLP-1(7-38) NH$_2$; (SEQ ID NO:16)
   - (Aib$^{8,35,37}$, Arg$^{34}$, Phe$^{31}$, D-His$^{38}$)hGLP-1(7-38) NH$_2$; (SEQ ID NO:19)
   - (Aib$^{8,35,37}$, Arg$^{34}$, Phe$^{31}$, Gly$^{38}$)hGLP-1(7-38) NH$_2$; (SEQ ID NO:20)
   - (Aib$^{8,35,37}$, Gly$^{38}$)hGLP-1(7-38) NH$_2$; (SEQ ID NO:21)
   - (Aib$^{8,35,37}$, Arg$^{26,34}$, Phe$^{31}$, D-His$^{38}$)hGLP-1(7-38) NH$_2$; (SEQ ID NO:22)
   - (Aib$^{8,35}$, Arg$^{26,34}$, Phe$^{31}$, β-Ala$^{37}$, D-His$^{38}$)hGLP-1(7-38) NH$_2$; (SEQ ID NO:23)
   - (Aib$^{8,35,37}$, Arg$^{26,34}$, Phe$^{31}$, β-Ala$^{38}$)hGLP-1(7-38) NH$_2$; (SEQ ID NO:24)
   - (Aib$^{8,35}$, Arg$^{26,34}$, Phe$^{31}$, β-Ala$^{37,38}$)hGLP-1(7-38) NH$_2$; (SEQ ID NO:25)
   - (Aib$^{8,35,37}$, Arg$^{34}$, Phe$^{31}$, β-Ala$^{38}$)hGLP-1(7-38) NH$_2$; (SEQ ID NO:26) or
   - (Aib$^{8,35,37}$, Arg$^{34}$, Phe$^{31}$, Gaba$^{38}$)hGLP-1(7-38) NH$_2$; (SEQ ID NO:27)

or a pharmaceutically acceptable salt thereof.

2. A pharmaceutical composition comprising a compound according to claim 1 or a pharmaceutically acceptable salt thereof and a pharmaceutically acceptable carrier or diluent.

* * * * *